United States Patent
Morré et al.

(10) Patent No.: US 6,410,052 B1
(45) Date of Patent: Jun. 25, 2002

(54) TEA CATECHINS IN SUSTAINED RELEASE FORMULATIONS AS CANCER SPECIFIC PROLIFERATION INHIBITORS

(75) Inventors: Dorothy M. Morré ; D. James Morré, both of West Lafayette, IN (US); Raymond Cooper, Mountain View; Michael N. Chang, Brisbane, both of CA (US)

(73) Assignees: Purdue Research Foundation, West Lafayette, IN (US); Pharmanex, Inc., Brisbane, CA (US)

( * ) Notice: Subject to any disclaimer, the term of this patent is extended or adjusted under 35 U.S.C. 154(b) by 0 days.

(21) Appl. No.: 09/637,840

(22) Filed: Aug. 10, 2000

Related U.S. Application Data

(63) Continuation-in-part of application No. 09/537,211, filed on Mar. 29, 2000.
(60) Provisional application No. 60/151,109, filed on Aug. 27, 1999, and provisional application No. 60/126,893, filed on Mar. 30, 1999.

(51) Int. Cl.[7] ........................... A61K 9/22; A61K 35/78; A61K 31/35; A61K 31/05
(52) U.S. Cl. ...................... 424/468; 424/729; 514/456; 514/732; 514/738
(58) Field of Search .............................. 424/468, 729; 514/456, 732, 738

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,391,568 A | 2/1995 | Chung |
| 5,591,767 A | 1/1997 | Mohr et al. |
| 5,605,810 A | 2/1997 | Morré et al. |
| 5,605,929 A * | 2/1997 | Liao et al. |
| 5,639,476 A | 6/1997 | Oshlack et al. |
| 5,674,533 A | 10/1997 | Santus et al. |
| 5,733,566 A | 3/1998 | Lewis |
| 5,866,158 A * | 2/1999 | Ribier et al. |
| 5,922,756 A * | 7/1999 | Chan |
| 5,955,269 A * | 9/1999 | Ghai et al. |
| 5,968,973 A | 10/1999 | Cheng et al. |
| 5,972,985 A * | 10/1999 | Thomas et al. |
| 5,989,557 A | 11/1999 | Bombardelli et al. |

FOREIGN PATENT DOCUMENTS

| | | |
|---|---|---|
| EP | 0 819 433 A | 1/1998 |
| JP | 2000119106 | 4/2000 |
| WO | WO 96/37201 A | 11/1996 |

OTHER PUBLICATIONS

Wang et al. 1994. Inhibitory Effects of Black Tea, Green Tea, Decaffeinated Black Tea, and Decaffeinated Green Tea on Ultraviolet B Light–induced Skin Carcinogenesis in 7,12–Dimethylbenz[a]anthracene–initiated SKH–1 Mice. Cancer Research 54:3428–3435.

Aucamp j. et al. 1997. Inhibition of xanthine oxidase by catechins from tea (*Camellia sinensis*). Anticancer Res. 17(6D):4381–5.

Hirose M, et al. 1994. Inhibition of mammary gland carcinogenesis by green tea catechins and other naturally occuring antioxidants in female Sprague–Dawley rats pretreated with 7,12–dimethylbenz[alpha]anthracene. Cancer Lett. 83(1–2):149–56.

Saeki K. et al. 1999. Apoptosis–inducing activity of polyphenol compounds derived from tea catechins in human histiolytic lymphoma U937 cells. Biosci Biotechnol Biochem. 63(3):585–7.

Tanaka H. et al. 1997. Post–initiation inhibitory effects of green tea catechins on 7,12–dimethylbenz[a]anthracene–induced mamary gland carcinogenesis in female Sprague–Dawley rats. Cancer Lett.116(1):47–52.

Ahmad et al., 1997, "Green tea constituent epigallocatechin–3–gallate and induction of apoptosis and cell cycle arrest in human carcinoma cells", J Natl Cancer Inst. 89(24):1881–6.

Ahmad et al., 1998, *Nutrition and Chemical Toxicity* (John Wiley and Sons, London) pp. 301–343.

Ahmad and Mukhtar, 1999, "Green tea polyphenols and cancer: biologic mechanisms and practical implications", Nutr Rev. 57(3):78–83.

Bridge et al., 1998, "Cancer–specific NADH oxidase (tNOX) a molecular target for the active principal of green tea?", Mol. Biol. Cell 9:84A.

Brightman et al., 1992, "A growth factor– and hormone–stimulated NADH oxidase from rat liver plasma membrane", Biochim Biophys Acta. 1105(1):109–17.

(List continued on next page.)

*Primary Examiner*—Christopher R. Tate
(74) *Attorney, Agent, or Firm*—Pennie & Edmonds LLP

(57) ABSTRACT

The invention described herein encompasses a methods and compositions of treating cancer or solid tumors comprising the administration of a therapeutically effective amount of catechins, a group of polyphenols found in green tea, to a mammal in need of such therapy. Compositions of catechins include but not limited to, epigallocatechin gallate (EGCg), epicatechin (EC), epicatechin gallate (ECG), epigallocatechin (EGC). The unique compositions of the invention contain various combinations of the catechins, alone or in combination with each other or other therapeutic agents and are used to treat primary and metastatic cancers in humans. The invention also encompasses the varying modes of administration of the therapeutic compounds, including a sustained release formulation which may be used as a therapeutic compound for the treatment of cancer or as a dietary supplement for the prevention of cancer.

30 Claims, 22 Drawing Sheets

OTHER PUBLICATIONS

Figure 1A:
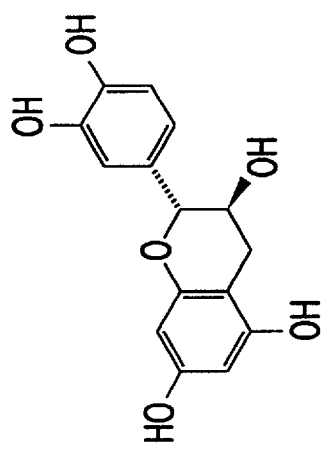
Figure 1B:
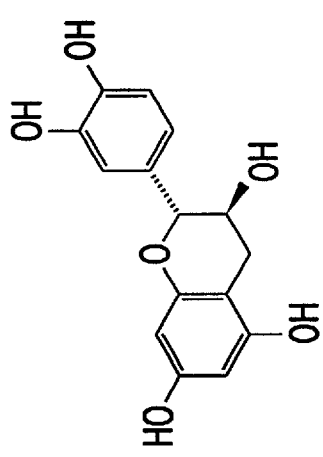
Figure 1C:
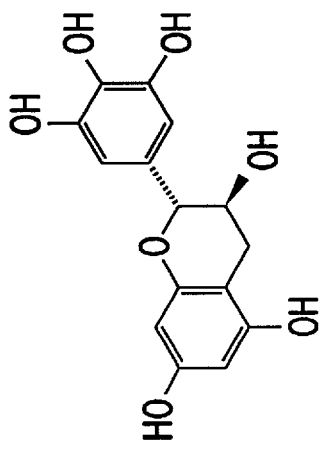
Figure 1D:
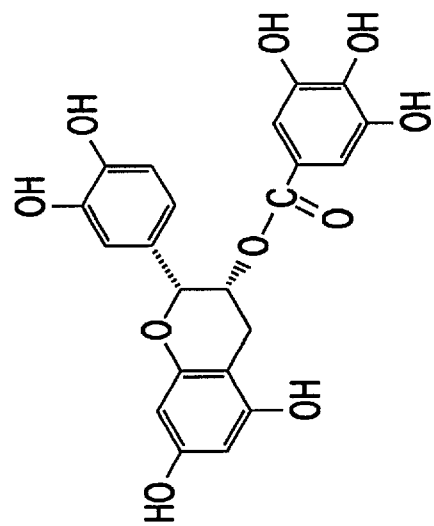
Figure 1E:
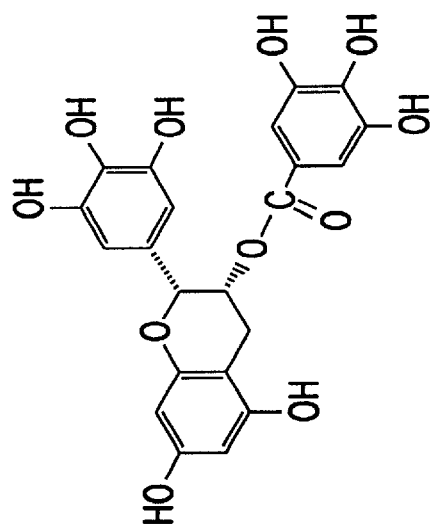
Figure 1F:
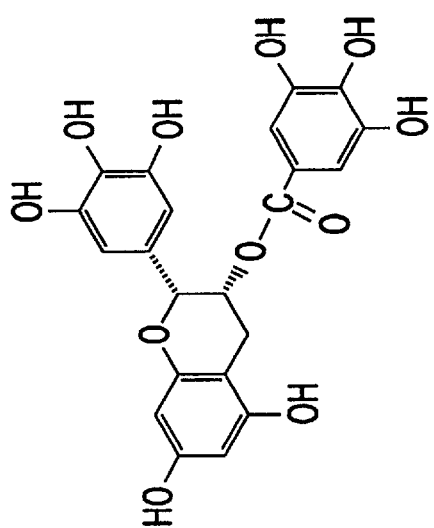

Bruno et al., 1992, "Stimulation of NADH oxidase activity from rat liver plasma membranes by growth factors and hormones is decreased or absent with hepatoma plasma membranes", Biochem J. 284 (Pt 3):625–8.

Chan et al., 1997, "Inhibition of inducible nitric oxide synthase gene expression and enzyme activity by epigallocatechin gallate, a natural product from green tea", Biochem Pharmacol. 54(12):1281–6.

Chen et al., 1998, "Green tea epigallocatechin gallate shows a pronounced growth inhibitory effect on cancerous cells but not on their normal counterparts", Cancer Lett. 129(2):173–9.

Chueh et al., 1997, "A 33.5–kDa heat– and protease–resistant NADH oxidase inhibited by capsaicin from sera of cancer patients", Arch Biochem Biophys. 342(1):38–47.

Chueh et al., 1998, "Isolation and expression cloning of a tumor–associated NADH oxidase (tNOX) that is a potential pancancer maker", Mol. Biol. Cell 9:184A.

DeHahn et al., 1997, "NADH oxidase activity present on both the external and internal surfaces of soybean plasma membranes", Biochim Biophys Acta 1328:99–108.

del Castillo–Olivares et al., 1998, "A drug–responsive and protease–resistant peripheral NADH oxidase complex from the surface of HeLa S cells", Arch Biochem Biophys. 358(1):125–40.

Dong et al., 1997, "Inhibition of tumor promoter–induced activator protein 1 activation and cell transformation by tea polyphenols, (–)–epigallocatechin gallate, and theaflavins", Cancer Res. 57(19):4414–9.

Fujiki et al., 1998, "Cancer inhibition by green tea", Mutat Res. 402(1–2):307–10.

Gershoff, 1997, "Why green tea may help fight cancer", Tufts University Health and Nutrition Letter 15(6):2.

Katiyar et al., 1992, "(–)–Epigallocatechin–3–gallate in *Camellia sinensis* leaves from Himalayan region of Sikkim: inhibitory effects against biochemical events and tumor initiation in Sencar mouse skin", Nutr Cancer 18(1):73–83.

Khan et al., 1988, "Inhibition of the skin tumorigenicity of (+/–)–7 beta,8 alpha–dihydroxy–9 alpha, 10 alpha–epoxy–7,8,9,10–tetrahydrobenzo[a]pyrene by tannic acid, green tea polyphenols and quercetin in Sencar mice", Cancer Lett. 42(1–2):7–12.

Kishi et al., 1999, "The plasma membrane NADH oxidase of HeLa cells has hydroquinone oxidase activity", Biochim Biophys Acta 1412(1):66–77.

Komori et al., 1993, "Anticarcinogenic activity of green tea polyphenols", Jpn J Clin Oncol 23(3):186–90.

Kuroda and Hara, 1999, "Antimutagenic and anticarcinogenic activity of tea polyphenols", Mutat Res. 436(1):69–97.

Leff, 1999, "Rheumatoid arthritis caves in afflicted mice drinking down antioxidant green–tea extract", BioWorld Today, Apr. 16.

Liang et al., 1997, "Suppression of extracellular signals and cell proliferation through EGF receptor binding by (–)–epigallocatechin gallate in human A431 epidermoid carcinoma cells", J Cell Biochem. 67(1):55–65.

Liao et al., 1995, "Growth inhibition and regression of human prostate and breast tumors in athymic mice by tea epigallocatechin gallate", Cancer Lett. 96(2):239–43.

Lin and Lin, 1997, "(–)–Epigallocatechin–3–gallate blocks the induction of nitric oxide synthase by down–regulating lipopolysaccharide–induced activity of transcription factor nuclear factor–kappaB", Mol Pharmacol. 52(3):465–72.

Morre et al., 1996, "Capsaicin inhibits plasma membrane NADH oxidase and growth of human and mouse melanoma lines", Eur J Cancer 32A(11):1995–2003.

Morre et al., 1995, "Capsaicin inhibits preferentially the NADH oxidase and growth of transformed cells in culture", Proc Natl Acad Sci U S A. 92(6):1831–5.

Morre, 1994, "Hormone– and growth factor–stimulated NADH oxidase", J Bioenerg Biomembr. 26(4):421–33.

Morre, 1998, *Plasma Membrane Redox Systems and their Role in Biological Stress and Disease* (Klewer Academic Publishers, The Netherlands).

Morre et al., 1997, "Is the drug–responsive NADH oxidase of the cancer cell plasma membrane a molecular target for adriamycin?", J Bioenerg Biomembr. 29(3):269–80.

Morre and Brightman, 1991, "NADH oxidase of plasma membranes", J Bioenerg Biomembr. 23(3):469–89.

Morre et al., 1995, "The antitumor sulfonylurea N–(4–methylphenylsulfonyl)–N'–(4–chlorophenyl) urea (LY181984) inhibits NADH oxidase activity of HeLa plasma membranes", Biochim Biophys Acta. 1240(1):11–7.

Nakachi et al., 1998, "Influence of drinking green tea on breast cancer malignancy among Japanese patients", Jpn J Cancer Res. 89(3):254–61.

Paschka et al., 1998, "Induction of apoptosis in prostate cancer cell lines by the green tea component, (–)–epigallocatechin–3–gallate", Cancer Lett. 130(1–2):1–7.

Piazza et al., 1995, "Antineoplastic drugs sulindac sulfide and sulfone inhibit cell growth by inducing apoptosis", Cancer Res. 55(14):3110–6.

Robbins and Angell, 1976, *Basic Pathology, 2d Ed.* (W.B. Saunders Co., Philadelphia) pp. 68–79.

Roitt et al., 1993, *Immunology, $3^{rd}$ Ed.* (Mosby, St. Louis) pp. 17.1–17.12.

Ruch et al., 1989, "Prevention of cytotoxicity and inhibition of intercellular communication by antioxidant catechins isolated from Chinese green tea", Carcinogenesis 10(6):1003–8.

Sadzuka et al., "Modulation of cancer chemotherapy by green tea", Clin Cancer Res. 4(1):153–6.

Stoner and Mukhtar, 1995, "Polyphenols as cancer chemopreventive agents", J Cell Biochem Suppl. 22:169–80.

Suganuma et al., 1996, "A new process of cancer prevention mediated through inhibition of tumor necrosis factor alpha expression", Cancer Res. 56(16):3711–5.

Suganuma et al., 1998, "Wide distribution of [3H](–)–epigallocatechin gallate, a cancer preventive tea polyphenol, in mouse tissue", Carcinogenesis 19(10):1771–6.

Suganuma et al., 1999, "Synergistic effects of (––)epigallocatechin with (––)–epicatechin, sulindac, or tamoxifen on cancer–preventive activity in the human lung cancer cell line PC–9", Cancer Res. 59(1):44–7.

Sugiyama and Sadzuka, 1998, "Enhancing effects of green tea components on the antitumor activity of adriamycin against M5076 ovarian sarcoma", Cancer Lett. 133(1):19–26.

Sun et al., 1987, "NADH diferric transferrin reductase in liver plasma membrane", J Biol Chem. 262(33):15915–21.

Wang et al., 1989, "Protection against polycyclic aromatic hydrocarbon–induced skin tumor initiation in mice by green tea polyphenols", Carcinogenesis 10(2):411–5.

Weisburger, 1997, "Tea and health: a historical perspective", Cancer Lett. 114(1–2):315.

Wright et al., 1994, "Inhibition of apoptosis as a mechanism of tumor promotion", FASEB J. 8(9):654–60.

Yang et al., 1998, "Inhibition of growth and induction of apoptosis in human cancer cell lines by tea polyphenols", Carcinogenesis 19(4):611–6.

Edgren et al., 1991, "Controlled Release Technology (Pharmaceutical)", *Encyclopedia of Chemical Technology*, vol. 7, $4^{th}$ edition (John Wiley and Sons, London) pp. 274–300.

Longer and Robinson, 1990, "Sustained–Release Drug Delivery Systems", *Remington's Pharmaceutical Sciences*, $18^{th}$ edition (Mack Pub. Co., Easton, PA) pp. 1676–1693.

* cited by examiner

TEA CATECHINS IN SUSTAINED RELEASE FORMULATIONS AS CANCER SPECIFIC PROLIFERATION INHIBITORS

This is a continuation-in-part of U.S. patent application no. 09/537,211, filed on Mar. 29, 2000, which is incorporated herein, by reference, in its entirety, and which in turn claims benefit to U.S. provisional application serial no. 60/126,893 filed Mar. 30, 1999 and U.S. provisional application serial no. 60/151,109 filed Aug. 27, 1999.

1. INTRODUCTION

The present invention relates to novel methods and sustained release compositions which utilize catechins, including but not limited to, epigallocatechin gallate (EGCg), epicatechin (EC), epicatechin gallate (ECG), and epigallocatechin (EGC), which are found in varying levels in tea leaves. The unique sustained release compositions of the invention contain various amounts of the catechins, including combinations of catechins, or catechins and other therapeutic agents. The invention also encompasses the varying modes of administration of the therapeutic compounds, such as a sustained release formulation which is used as a therapeutic compound for the treatment of cancer or as a dietary supplement for the prevention of cancer.

2. BACKGROUND OF THE INVENTION

Tea is generally in the form of black, oolong, and green tea, all originating from the tea plant, *Camellia sinensis*. Tea is cultivated in approximately thirty countries worldwide, and is consumed globally. Although the level of tea consumption varies around the world, it is believed that tea consumption is second only to water (Ahmad et al., 1998, Nutrition and Chemical Toxicity, John Wiley and Sons, Sussex, England, pp. 301–343). Black tea is consumed predominantly in Western and some Asian countries and green tea is consumed predominantly in China, Japan, India, and a few countries in North Africa and the Middle East (Ahmad et al., 1998, Nutrition and Chemical Toxicity, John Wiley and Sons, Sussex, England, pp. 301–343).

Green tea has been prized as a traditional tonic and has been widely consumed in East Asia. Recent studies have attempted to link green tea to antioxidant benefits including protection against the damage caused by cigarette smoke, pollution, stress, and other toxins (for an overview, see e.g., Mitscher, 1998, The Green Tea Book, Avery Publishing Group, Garden City Park, N.Y. and Weisburger, 1997, Can. Lett. 114:315–317).

An empirical link between green tea and its cancer prevention properties was made in the late 1980s (Khan et al., 1988, Can. Lett. 42:7–12 and Wang et al., 1989, Carcinogenesis 10:411–415). Epidemiological studies show that cancer onset of patients in Japan who had consumed ten cups of green tea per day was 8.7 years later among females and 3 years later among males, compared with patients who had consumed under three cups per day (Fujiki et al., 1998, Mutation Res. 402:307–310). As such, a possible relationship between high consumption of green tea and low incidence of prostate and breast cancer in Asian countries where green tea consumption is high has been postulated (Liao et al., 1995, Can. Lett. 96:239–243 and Stoner and Mukhtar, 1995, J. Cell. Biochem. 22:169–180). However, because of the many variables in lifestyle inherent to such a study, a definitive link between green tea and its cancer prevention effects could not be concluded.

Scientists have now identified many of the natural substances in green tea that may provide the majority of its health benefits. One class of chemicals that has attracted much study is the polyphenols, also known as catechins.

2.1. Epigallocatechin Gallate (EGCg)

The polyphenols describe a class of substituted phenolic compounds that are known as flavanols or catechins. The polyphenols in green tea that have been identified are catechin (C), epicatechin (EC), gallocatechin (GC), gallocatechin gallate (GCG), epigallocatechin (EGC), epicatechin gallate (ECG), and epigallocatechin gallate (EGCg) (FIG. 1). In addition, caffeine, theobromine, theophylline, and phenolic acids, such as gallic acid, are also present as constituents of green tea in smaller quantities than the polyphenols (Ahmad et al., 1998, Nutrition and Chemical Toxicity, John Wiley and Sons, Sussex, England, pp. 301–343).

Epigallocatechin gallate (EGCg), the major catechin in green tea, has been the focus of many studies to determine if it is responsible for the antioxidant and anticarcinogenic effects of green tea, as reviewed by Ahmad and Mukhtar, 1999, Nutr. Rev. 57:78–83. The administration of a pharmacologically effective amount of EGCg has been alleged to reduce the incidence of lung cancer in a mammal (U.S. Pat. No. 5,391,568). A bioavailability study showed that frequent green tea consumption results in high levels of EGCg in various body organs, suggesting that green tea consumption may protect against cancers localized to different sites of the body (Sugunama et al., 1998, Carcinogenesis 19:1771–1776).

EGCg has been implicated in blocking DNA transcription of a number of genes in cancer cell lines. For example, in the human epidermal carcinoma cell line A431, EGCg inhibits the DNA and protein synthesis of the growth factor receptors epidermal growth factor receptor (EGF-R), platelet-derived growth factor receptor (PDGF-R), and fibroblast growth factor receptor (FGF-R) (Liang et al., 1997, J. Cell. Biochem. 67:55–65). EGCg has also been implicated in blocking transcription of nitric oxide (NO) synthase by inhibiting the binding of transcription factor NFκB to the NO synthase promotor (Lin and Lin, 1997, Mol. Pharmacol. 52:465–472 and Chan et al., 1997, Biochem. Pharmacol. 54:1281–1286). In the tumor cell line JB6, EGCg inhibits AP-1 transcriptional activity (Dong et al., 1997, Can. Res. 57:4414–4419). These results suggest that EGCg may prevent cancer at the level of gene transcription, i.e., by blocking the DNA synthesis of genes involved in signal transduction pathways.

Further, the focus of many other studies has been the effect of EGCg on apoptosis, or programmed cell death. Apoptosis differs from necrosis, and is regarded as an ideal mechanism for the elimination of cells. Studies have shown that several anti-cancer preventative agents may induce apoptosis, and conversely, several tumor-promoting agents inhibit apoptosis (Wright et al., 1994, FASEB J 8:654–660 and Ahmad and Mukhtar, 1999, Nutr. Rev. 57:78–83).

Much of the prior work in the art has attempted to determine what, if any, effect EGCg has on the growth inhibition and apoptosis induction of cancer cells. A differential growth inhibitory effect was reported in human colorectal cancer cells CaCo-2, breast cancer cells Hs578T, and their non-cancer cell counterparts (Ahmad and Mukhtar, 1999, Nutr. Rev. 57:78–83). EGCg has been implicated in the growth arrest and subsequent induction of apoptosis following cell growth inhibition has been shown in virally transformed fibroblast cells W1138, human epidermal carcinoma cells A431, lung cancer tumor cells H611, prostate cancer cell lines LNCaP, PC-3, and DU145, human carcinoma keratinocytes HaCaT, and mouse lymphoma cells LY-R (Chen et al., 1998, Can. Lett. 129:173–179; Ahmad et al., 1997, J. of the Nat. Can. Inst. 89:1881–1886; Yang et al., 1998, Carcinogenesis 19:611–616; Paschka et al., 1998, Can. Lett. 130:1–7; and Ahmad and Mukhtar, 1999, Nutr. Rev. 57:78–83). In studies where the apoptotic response was studied in cancer cells versus their non-cancer counterparts, e.g., human carcinoma keratinocytes HaCaT versus normal human epidermal keratinocytes, the apoptotic response to EGCg was reported to be specific to the cancer cells (Ahmad et al., 1997, J. Nat. Can. Inst. 89:1881–1886).

It has been suggested that EGCg induced apoptosis may result from either cell cycle arrest and/or $H_2O_2$ production (Ahmad et al., 1997, J. Nat. Can. Inst. 89:1881- 1886; Fujiki et al., 1998, Mutat. Res. 402:307–310; and Yang et al., 1998, Carcinogenesis 19:611–616). EGCg may be involved in the growth regulation of human epidermal carcinoma cells A431 by causing cell cycle arrest of the $G_0$ to $G_1$ phase (Ahmad et al., 1997, J. Nat. Can. Inst. 89:1881–1886). EGCg has also been implicated in phase arrest between $G_2$ to M phase of the cell cycle in human lung cancer cells (Fujiki et al., 1998, Mutat. Res. 402:307–310). In the EGCg induced inhibition of human lung cancer cells, it was suggested that the tumor necrosis factor (TNF) α pathway that is the mode of action of EGCg. Alternatively, the EGCg-induced apoptosis of the lung cancer tumor cells H611 is inhibited by catalase, suggesting the $H_2O_2$ production as a probable cause of apoptosis (Yang et al., 1998, Carcinogenesis 19:611–616).

Despite the above studies, the efficacy of EGCg as a single agent therapy for the prevention of cancer is still unclear. Moreover, the efficacy of EGCg as a therapeutic drug to treat or reverse cancer in a patient is unknown.

2.2. Other Catechins and Combinations Thereof

Although the focus of much of the prior research has been on EGCg, the putative biological functions of some of the other catechins has been examined. For example, both epicatechin gallate (ECG) and epigallocatechin (EGC) have been reported to be as effective as EGCg in inducing apoptosis of human epidermal carcinoma cells A431 at similar concentrations, whereas epicatechin (EC) did not show a similar effect (Ahmad et al., 1997, J. of the Nat. Can. Inst. 89:1881–1886). Growth inhibition in lung tumor cell lines H661 and H1299 was also observed with EGCg and EGC, whereas ECG and EC were less effective (Yang et al., 1998, Carcinogenesis 19:611–616).

Catechins have been implicated in growth inhibition of the human lung cancer cell line PC-9, with the order of catechin potency being reported as EGCg=ECG>EGC>EC (Okabe et al., 1993, Jpn. J. Clin. Oncol. 23:186–190). It has also been demonstrated that catechin combinations of EGCg and EC, ECG and EC, and EGC and EC induce apoptosis of the human lung cancer cell line PC-9 in vitro (Suganuma et al., 1999, Can. Res. 59:44–47). EC is thought to enhance incorporation of EGCg into the cells, which is thought to inhibit TNF a release resulting in the induction of apoptosis (Suganuma et al., 1999, Can. Res. 59:44–47).

Green tea extract, an important source of EGCg, has previously been reported to enhance the effect of the anticancer agents, e.g., adriamycin and doxorubicin (Sugiyama and Sadzuka, 1998, Can. Lett. 133:19–26 and Sadzuka et al., 1998, Clin. Can. Res. 4:153–156). Green tea in combination with adriamycin inhibits tumor growth in M5076 ovarian sarcoma cells, whereas adriamycin alone does not inhibit tumor growth in M5076 ovarian sarcoma cells (Sugiyama and Sadzuka, 1998, Can. Lett. 133:19–26). A similar effect is observed with green tea extract and doxorubicin on the same M5076 ovarian sarcoma cell line. Green tea extract, in combination with doxorubicin, also enhances the inhibitory growth effect on Ehrlich ascites carcinoma tumors in tumor-bearing mice, presumably by increasing the concentration of doxorubicin concentration in the tumor, but not in normal tissue (Sadzuka et al., 1998, Clin. Can. Res. 4:153–156).

EGCg has also been shown to enhance the effect of cancer prevention drugs in vitro. For example, EGCg has been shown to enhance the apoptotic effect of sulindac and tamoxifin, presumably by EGCg enhancing the intracellular concentration of the cancer prevention drugs. (Suganuma et al., 1999, Can. Res. 59:44–47). Both sulindac and tamoxifin induce apoptosis of human cancer cells and inhibit TNF α release from BALB/c-3T3 cells (Piazza et al., 1995, Can. Res. 55:3110–3116; Chen et al., 1996, J. Cell. Biochem. 61:9–17; and Sugunama et al., 1996, Can. Res. 56:3711–3715).

2.3. NADH Oxidase

A unique plasma membrane NADH oxidase (NOX), a unique cell surface protein with hydroquinone (NADH) oxidase and protein disulfide-thiol interchange activities that is responsive to hormone and growth factors has been identified (Brightman et al., 1992, Biochim. Biophys. Acta 1105:109–117; Morré, 1994, J. Bioenerg. Biomemb. 26:421–433; and Morré, 1998, Plasma Membrane Redox Systems and their Role in Biological Stress and Disease, Klewer Academic Publishers, Dordrecht, The Netherlands, pp. 121–156). Further, a hormone-insensitive and drug-responsive form of NOX designated tNOX which is specific to cancer cells has been reported (Bruno et al., 1992, Biochem. J. 284:625–628; Morré and Morré, 1995, Protoplasma 184:188–195; Morré et al., 1995, Proc. Natl. Acad. Sci. U.S.A. 92;1831–1835; Morré et al., 1995, Biochim. Biophys. Acta 1240:11–17; Morré et al., 1996, Eur. J. Can. 32A: 1995–2003; and Morré et al., 1997, J. Biomemb. Bioenerg. 29:269–280).

Because the NOX protein is located at the external plasma membrane surface and is not transmembrane, a functional role as an NADH oxidase is not considered likely (Morré, 1994, J. Bioenerg. Biomemb. 26:421–433; DeHahn et al., 1997, Biochim. Biophys. Acta 1328:99–108; and Morré, 1998, Plasma Membrane Redox Systems and Their Role in Biological Stress and Disease, Klewer Academic Publishers, Dordrecht, The Netherlands, pp. 121–156). While the oxidation of NADH provides a basis for a convenient method to assay the activity, the ultimate electron physiological donor is most probably hydroquinones with specific activities for hydroquinone oxidation greater than or equal to that of NADH oxidation and/or protein thiol-disulfide interchange (Kishi et al., 1999, Biochim. Biophys. Acta 1412:66–77).

CNOX was originally defined as a drug-indifferent constitutive NADH oxidase activity associated with the plasma membrane of non-transformed cells that was the normal counterpart to tNOX (Morré, 1998, Plasma Membrane Redox Systems and Their Role in Biological Stress and Disease, Kiewer Academic Publishers, Dordrecht, The Netherlands, pp. 121–156). Indeed, a 36 kD protein isolated from rat liver and from plants has NOX activity that is unresponsive to tNOX inhibitors (Brightman et al., 1992, Biochim. Biophys. Acta 1105:109–117).

While cancer cells exhibit both drug-responsive and hormone and growth factor-indifferent (tNOX) as well as drug inhibited and hormone and growth factor dependent (CNOX) activities, non-transformed cells exhibit only the drug indifferent hormone- and drug-responsive CNOX. Among the first descriptions of so-called constitutive or CNOX activity of non-transformed cells and tissues was where the activity of rat liver plasma membranes was stimulated by the growth factor, diferric transferrin (Sun et al., 1987, J. Biol. Chem. 262:15915–15921). Subsequent work demonstrated that the observed NADH oxidation was catalyzed by a unique enzyme exhibiting responsiveness to several hormones and growth factors (Bruno et al., 1992, Biochem J. 284:625–628). Unlike mitochondrial oxidases, the hormone-stimulated NADH oxidase activity of rat liver plasma membranes is not inhibited by cyanide (Morré, 1994, J. Bioenerg. Biomemb. 26:421–433). The enzyme also was distinguished from other oxidase activities by its response to several common oxidoreductase inhibitors, e.g., catalase, azide and chloroquine, as well as to various detergents e.g., sodium cholate, Triton X-100 and CHAPS (Morré and Brightman, 1991, J. Bioenerg. Biomemb. 23:469–489 and Morré et al., 1997, J. Biomemb. Bioenerg. 29:269–280). Like tNOX of cancer cells, CNOX is a unique membrane-associated protein that is capable of oxidizing NADH but has an activity which is modulated by hormones and growth factors.

2.4. Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W.B. Saunders Co., Philadelphia, pp. 68–79) Hyperplasia is a form of controlled cell proliferation involving an increase in cell number in a tissue or organ, but without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, Brostoff, and Kale, 1993, Immunology, 3rd ed., Mosby, St. Louis, pp. 17.1–17.12).

There remains a need for treatment of cancer that does not have the adverse effects generally caused by non-selectivity, of conventional chemotherapeutic agents. None of the above studies, which are not to be construed as an admission that any of the above studies is prior art, have suggested the present mechanism by which the catechins are able to differentiate between cancer and non-cancer cells. Moreover, none of the studies evaluated the efficacy of varying levels of catechin combinations or compositions of multiple catechins for the treatment of cancer. In contrast, the Inventors have identified a cancer-specific isoform of a unique plasma membrane NADH oxidase (tNOX) which is inhibited by the catechins. Furthermore, the studies cited supra have hypothesized that EGCg mediates its effects intracellularly, since EGCg incorporation into the cell seems to be a prerequisite for the inhibition of TNF α release. Inhibition of tNOX, an extracellular membrane-associated protein) by EGCg, and synergistically with other catechins and anti-cancer agents, results in the selective inhibition of cancer cell growth and ultimately, apoptosis. Further discussion of catechin-induced apoptosis wherein tNOX is targeted is presented in Sections 6, 7, and 8.

3. SUMMARY OF THE INVENTION

The invention encompasses sustained release formulations comprising catechins, a group of polyphenols found in green tea, which are used as therapeutic compounds for the treatment of cancer or as a dietary supplement that offers white blood cell protection and maintains healthy blood levels, all of which suggests that the catechins play a role in the prevention of cancer. The sustained release compositions optimally maintain circulating levels of said composition in the body at a certain threshold level over an extended time period. Specific therapeutic regimens, pharmaceutical compositions, and kits are also provided by the invention.

In one embodiment, the invention described herein comprises the administration of catechins in a sustained release formulation to a mammal as a dietary supplement for the prevention of cancer. In a preferred embodiment, the mammal is a human.

In one embodiment, the invention described herein comprises the administration of a therapeutically effective amount of catechins in a sustained release formulation to a mammal in need of such therapy. In a preferred embodiment, the mammal is a human. In another embodiment, the invention further encompasses the use of combination therapy to treat cancer.

In a specific embodiment, the catechins comprise epigallocatechin gallate (EGCg), epicatechin gallate (ECG), epigallocatechin (EGC), and epicatechin (EC) or a combination thereof, optionally in combination with other polyphenols.

The disclosure is based, in part, on the discovery that epigallocatechin gallate (EGCg), alone and in combination with other catechins and other anti-cancer therapeutic agents, inhibits the activity of a cancer-specific protein, an isoform of NADH oxidase specific to cancer cells (tNOX). The inhibition of tNOX results in the inhibition of cell growth, and ultimately, apoptosis of the cancer cell, whereas normal cells (which lack tNOX but instead express the isoform CNOX) are less affected. Thus, the invention provides a potent therapeutic effect without or while reducing the adverse effects on normal, healthy cells.

Significantly the effect of the catechins such as EGCg is reversible, i.e., if the EGCg is removed, cancer cells resume normal rates of growth. Other discoveries include: (1) EGCg is rapidly cleared from the blood and metabolized, (2) cancer cells must be inhibited from growing for 48 to 72 hours before EGCg-induced apoptosis occurs, and (3) when cancer cells are challenged with $10^{-7}$ M EGCg every two hours during the day, their growth is inhibited, but during the night normal cell growth resumes in the absence of further EGCg addition. Thus, the invention is directed to the administration of sustained release formulations so that a constant level of the catechins is maintained.

Particular compositions of the invention and their uses are described in the sections and subsections which follow.

3.1. Definitions

As used herein, the term "cancer" describes a diseased state in which a carcinogenic agent or agents causes the transformation of a normal cell into an abnormal cell, the invasion of adjacent tissues by these abnormal cells, and lymphatic or blood-borne spread of malignant cells to regional lymph nodes and to distant sites, i.e., metastasis.

As used herein, the terms "preventing cancer" and "prevention of cancer" mean to inhibit the transformation of a normal cell into an abnormal cell by a carcinogenic agent or agents and/or to inhibit the accumulation of cells expressing cancer-specific genes (e.g., tNOX) to a number which creates clinical symptoms associated with cancer.

As used herein, the terms "treating cancer" and "treatment of cancer" mean to inhibit the replication of cancer cells, to inhibit the spread of cancer, to decrease tumor size, to lessen or reduce the number of cancerous cells in the body, and to ameliorate or alleviate the symptoms of the disease caused by the cancer. The treatment is considered therapeutic if there is a decrease in mortality and/or morbidity.

The term "synergistic" as used herein refers to a combination which is more effective than the additive effects of any two or more single agents. A determination of a synergistic interaction between catechins, and another therapeutic agent may be based on the results obtained from the NOX assays described in Section 5.4 infra. The results of these assays are analyzed using Chou and Talalay's combination method and Dose-Effect Analysis with Microcomputers' software in order to obtain a Combination Index (Chou and Talalay, 1984, Adv. Enzyme Regul. 22:27–55 and Chou and Chou, 1987, software and manual, Elsevier Biosoft, Cambridge, UK, pp. 19–64). Combination Index values <1 indicates synergy, values >1 indicate antagonism and values equal to 1 indicate additive effects.

The term "pharmaceutically acceptable carrier" refers to a carrier medium that does not interfere with the effectiveness of the biological activity of the active ingredient, is chemically inert and is not toxic to the patient to whom it is administered.

The term "pharmaceutically acceptable salts" refers to salts prepared from pharmaceutically acceptable non-toxic acids and bases, including inorganic and organic acids and bases.

As used herein the term "pharmaceutically acceptable derivative" refers to any homolog, analog, or fragment corresponding to the catechin formulations as described in Section 5.1 infra which exhibits anti-cancer activity and is relatively non-toxic to the subject.

The term "therapeutic agent" refers to any molecule, compound or treatment that assists in the treatment of a cancer or the diseases caused thereby.

As used herein, the term "sustained release formulation" refers to any composition that provides slow, controlled, and/or timed release of one or more active ingredients.

The catechins and target proteins defined herein are abbreviated as follows:

| | |
|---|---|
| (±) - catechin | C |
| (−) - epicatechin | EC |
| gallocatechin | GC |
| gallocatechin gallate | GCG |
| (−) - epigallocatechin | EGC |
| (−) - epicatechin gallate | ECG |
| (−) - epigallocatechin gallate | EGCg |
| nicotinamide adenine dinucleotide | NADH |
| cell surface hydroquinone (NADH) oxidase with protein disulfide - thiol isomerase activity | NOX |
| NOX present in both non-cancer and cancer cells | CNOX |
| NOX specific to cancer cells | tNOX |

4. BRIEF DESCRIPTION OF THE DRAWINGS

FIGS. 1A–1F. Structures of six catechins from green tea. A. (±)-catechin (C). B. (−) epicatechin (EC). C. (−)-epigallocatechin (EGC). D. (−)-epicatechin gallate (ECG). E. (−)-epigallocatechin gallate (EGCg). F. (−)-gallocatechin gallate (GCG)

FIGS. 2A–2D. Dose-response of NADH oxidase of isolated plasma membranes (A, B) and growth of attached cells (C, D) to (−)-epigallocatechin gallate (EGCg). A, C. MCF-10A human mammary epithelial (non-cancer) cells (●) and BT-20 human mammary adenocarcinoma (cancer) cells (○). B, D. HeLa (human cervical carcinoma) cells. Values are averages of duplicate determinations in each of three separate experiments (n=6) ± standard deviations among experiments (n=3).

Figure 2A:
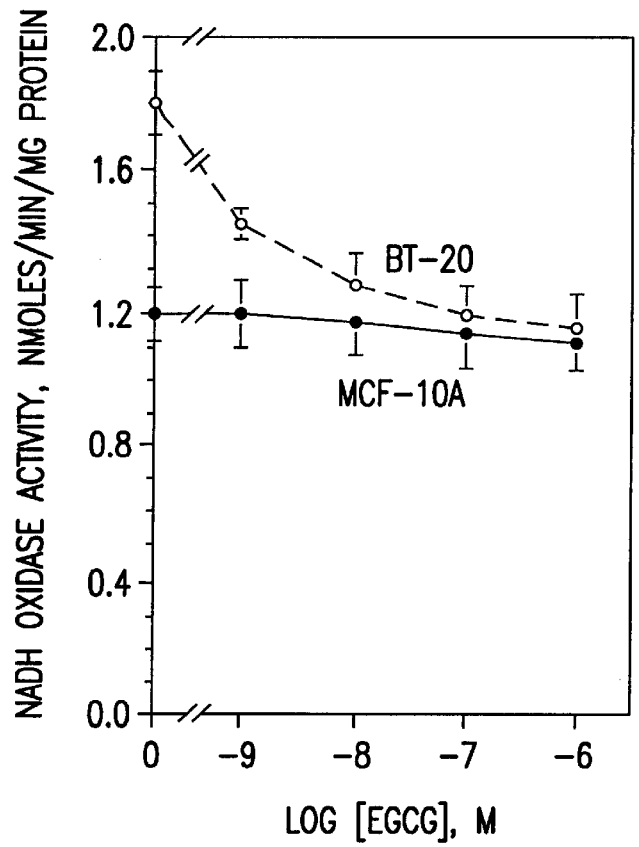
Figure 2B:
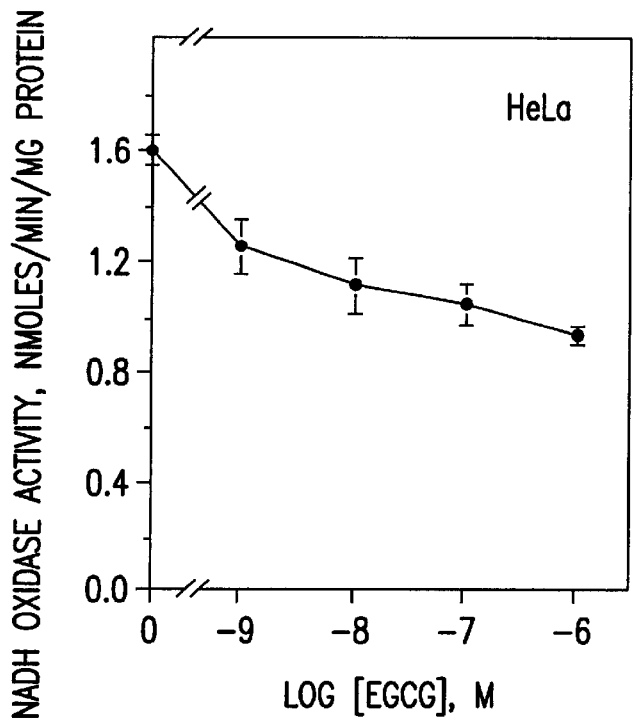
Figure 2C:
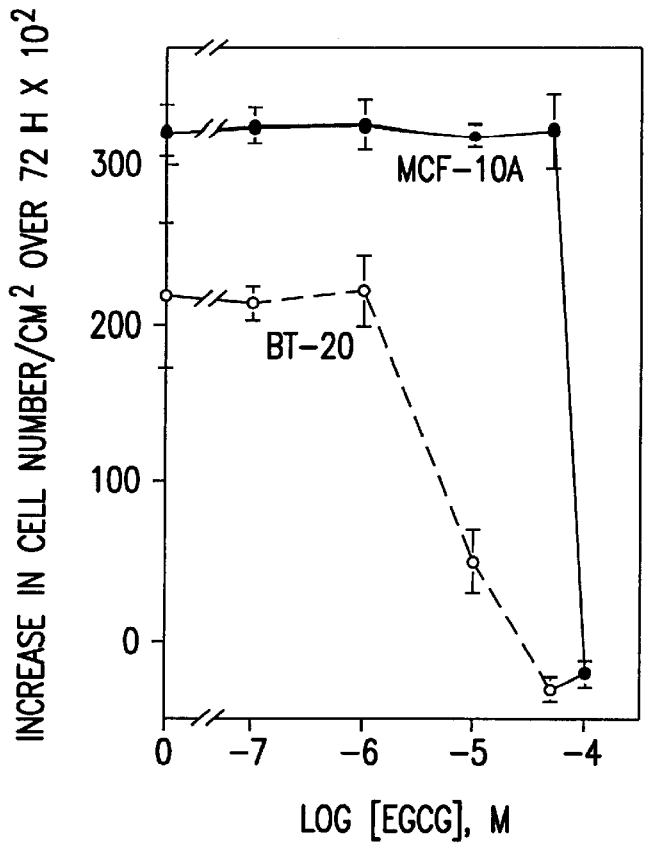
Figure 2D:
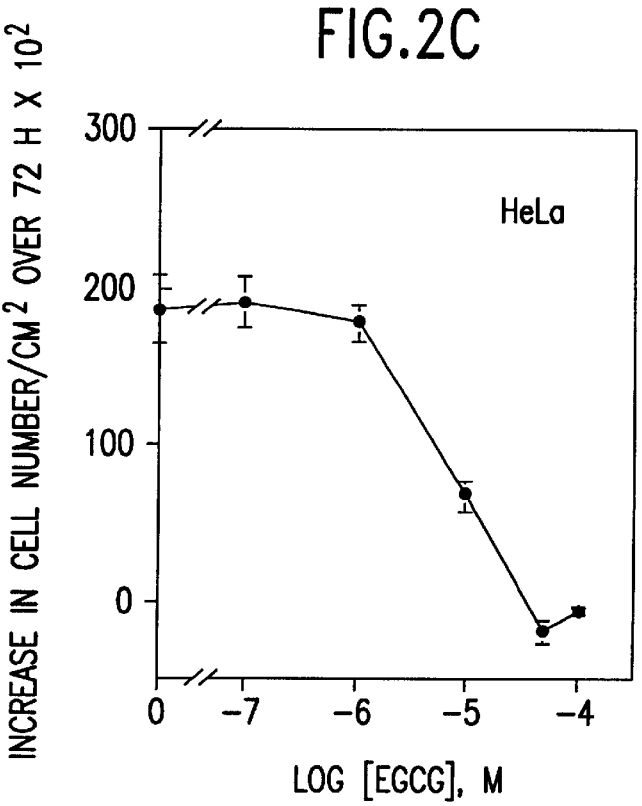
Figure 3B:
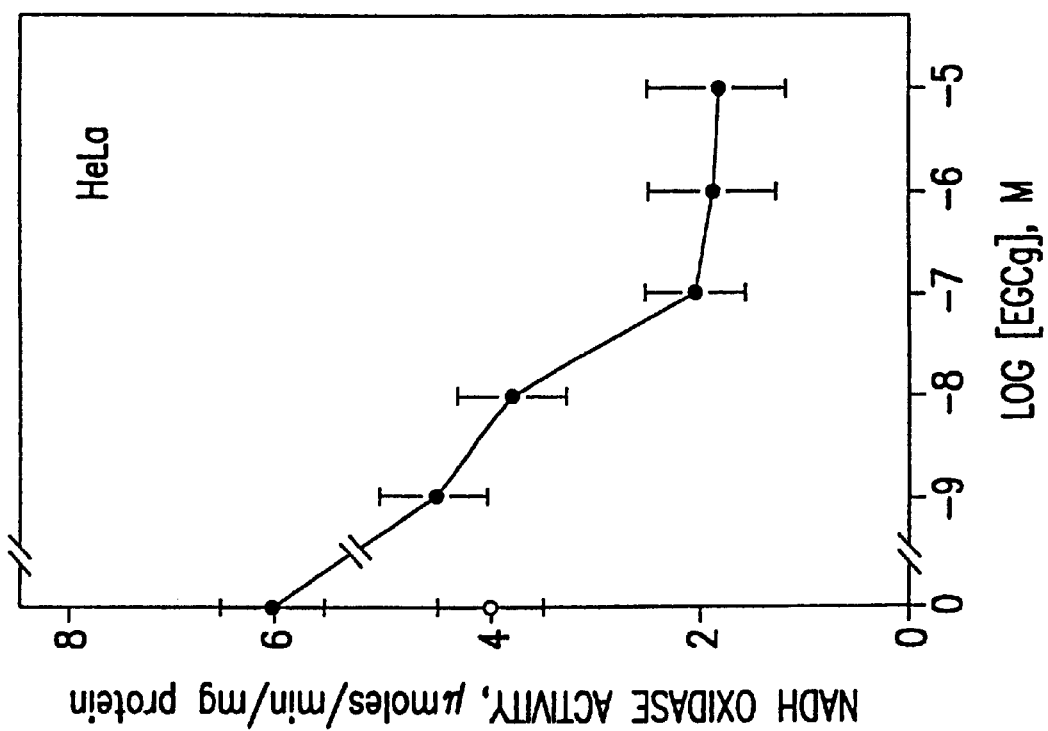
Figure 3A:
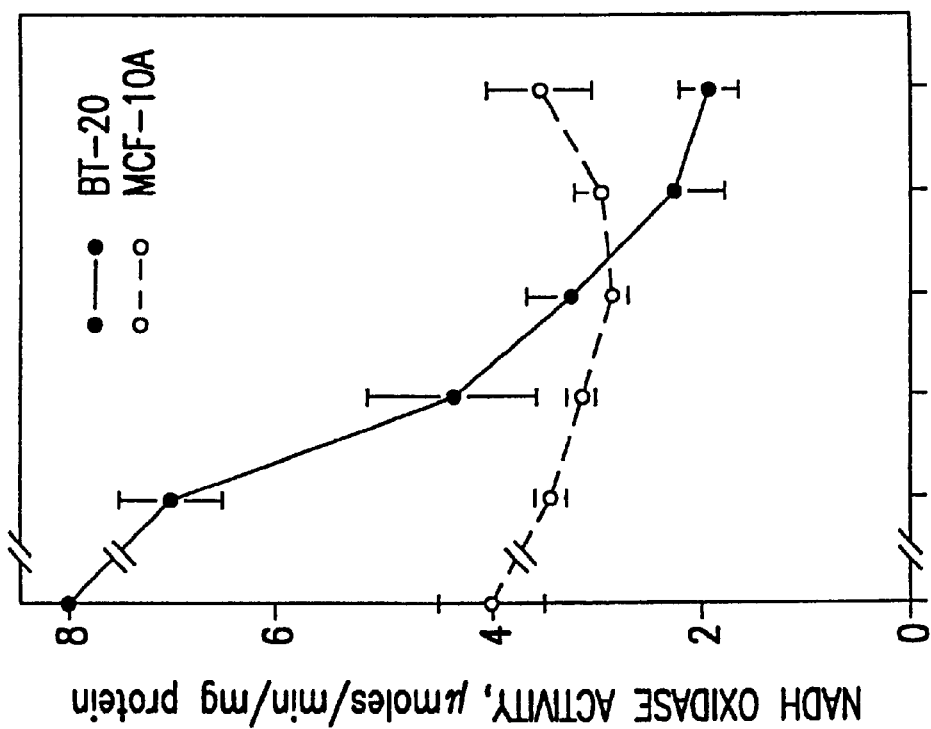

FIGS. 3A–3B. Dose-response of solubilized and partially purified NADH oxidase to (−)-epigallocatechin gallate (EGCg). A. NADH oxidase from MCF-10A and BT-20 cells. B. NADH oxidase from HeLa cells. As with plasma membranes (FIG. 2), the preparations from BT-20 and HeLa cells contained NOX activities both susceptible and resistant to inhibition by EGCg whereas the preparations from MCF10A cells was resistant to inhibition. Results are averages of duplicate determinations in each of three separate experiments (n=6) ± standard deviations among experiments (n=3).

Figure 4:
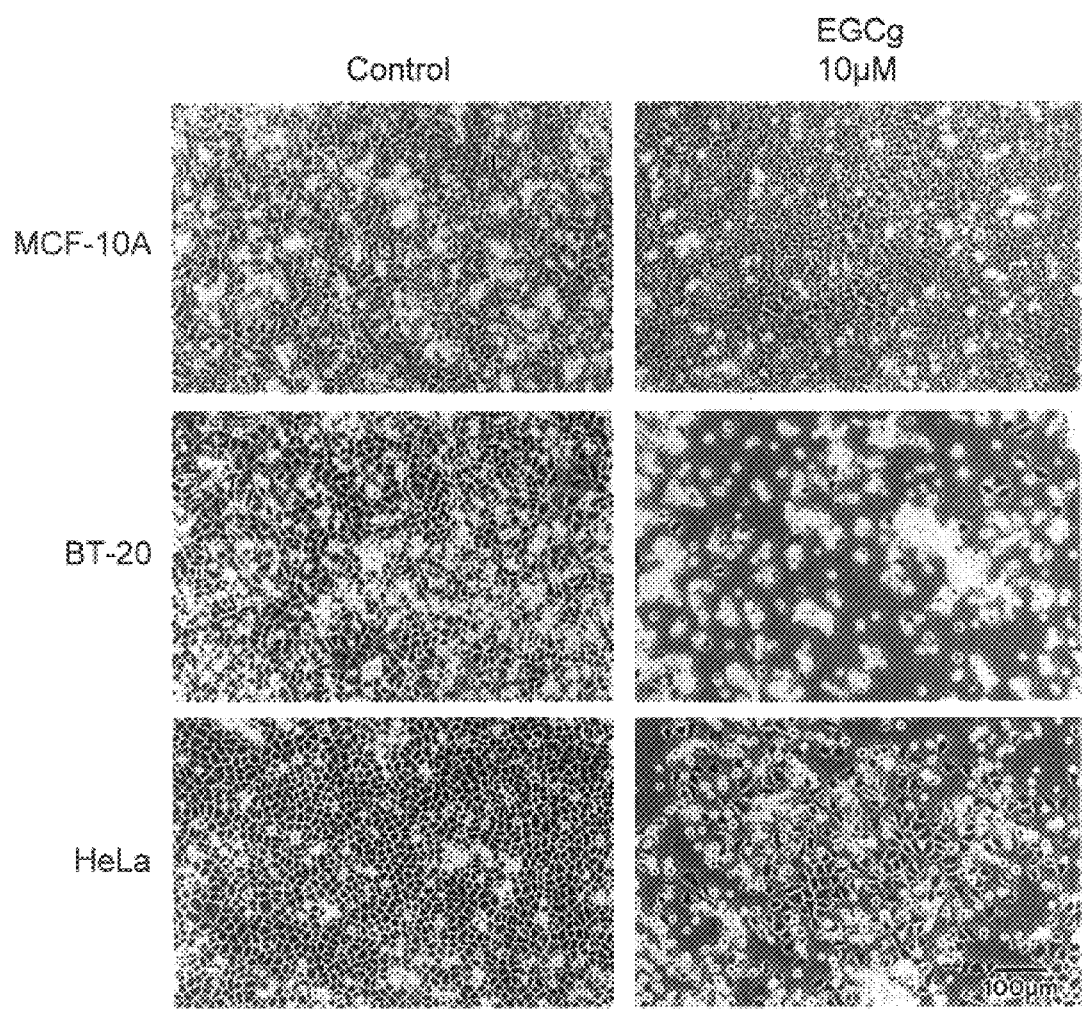

FIG. 4. Photomicrographs of MCF-10A mammary epithelial (non-cancer), BT-20 mammary adenocarcinoma and HeLa cells treated for 96 h with 10 μM (−)-epigallocatechin gallate (EGCg) added at t=0. The BT-20 and HeLa cells stopped growing and died whereas the MCF-10 cells recovered fully.

Figure 5:
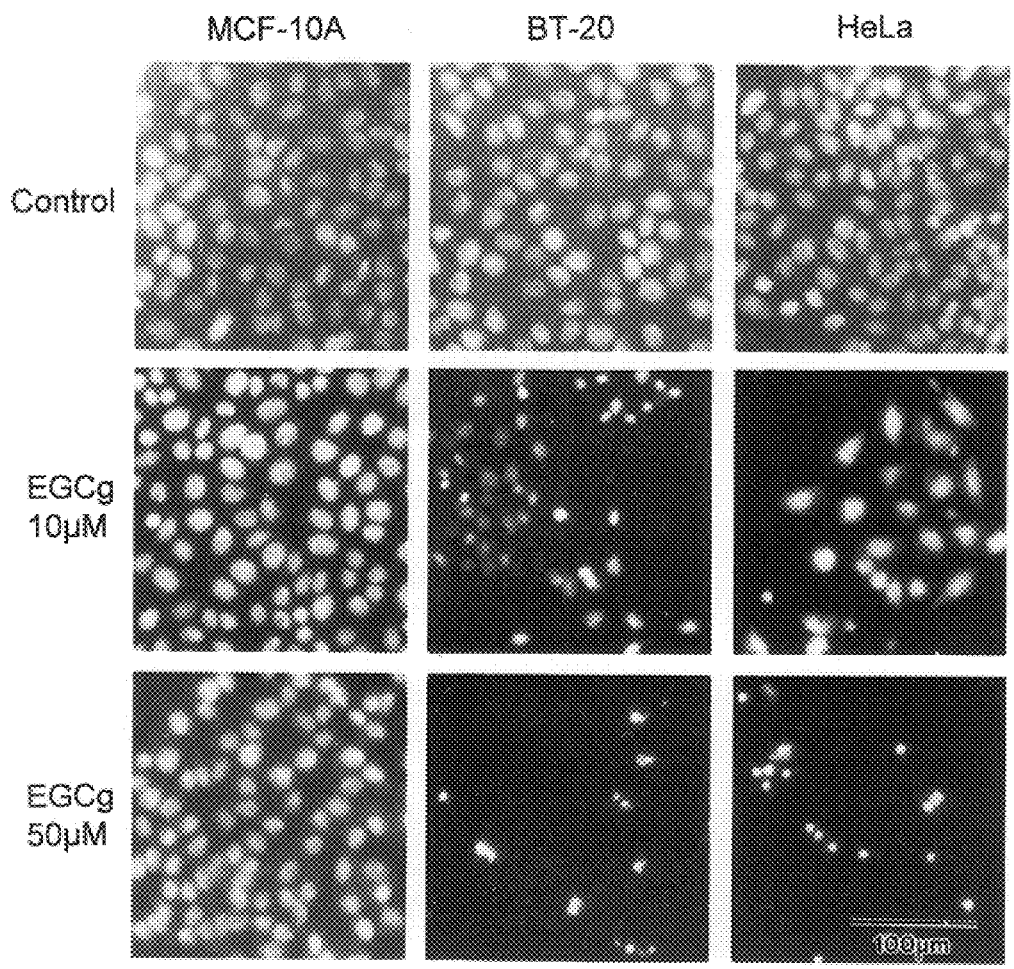

FIG. 5. Photomicrographs of MCF-10A, BT-20 and HeLa cells stained with 4', 6-diamidino-2-phenylindole (DAPI) (Wolvetang et al., 1994, FEBS Lett. 339:40–44) to show condensed chromatin after 96 h in the presence of 10 or 50 μM epigallocatechin gallate (EGCg) characteristic of apoptosis for BT-20 and HeLa but not for MCF-10A cells. Cells were grown on coverslips in the absence (upper panel) or presence (lower 2 panels) of 10 or 50 μM EGCg and fixed. Nuclear DNA was stained with DAPI and analyzed with a fluorescence microscope.

Figure 6:
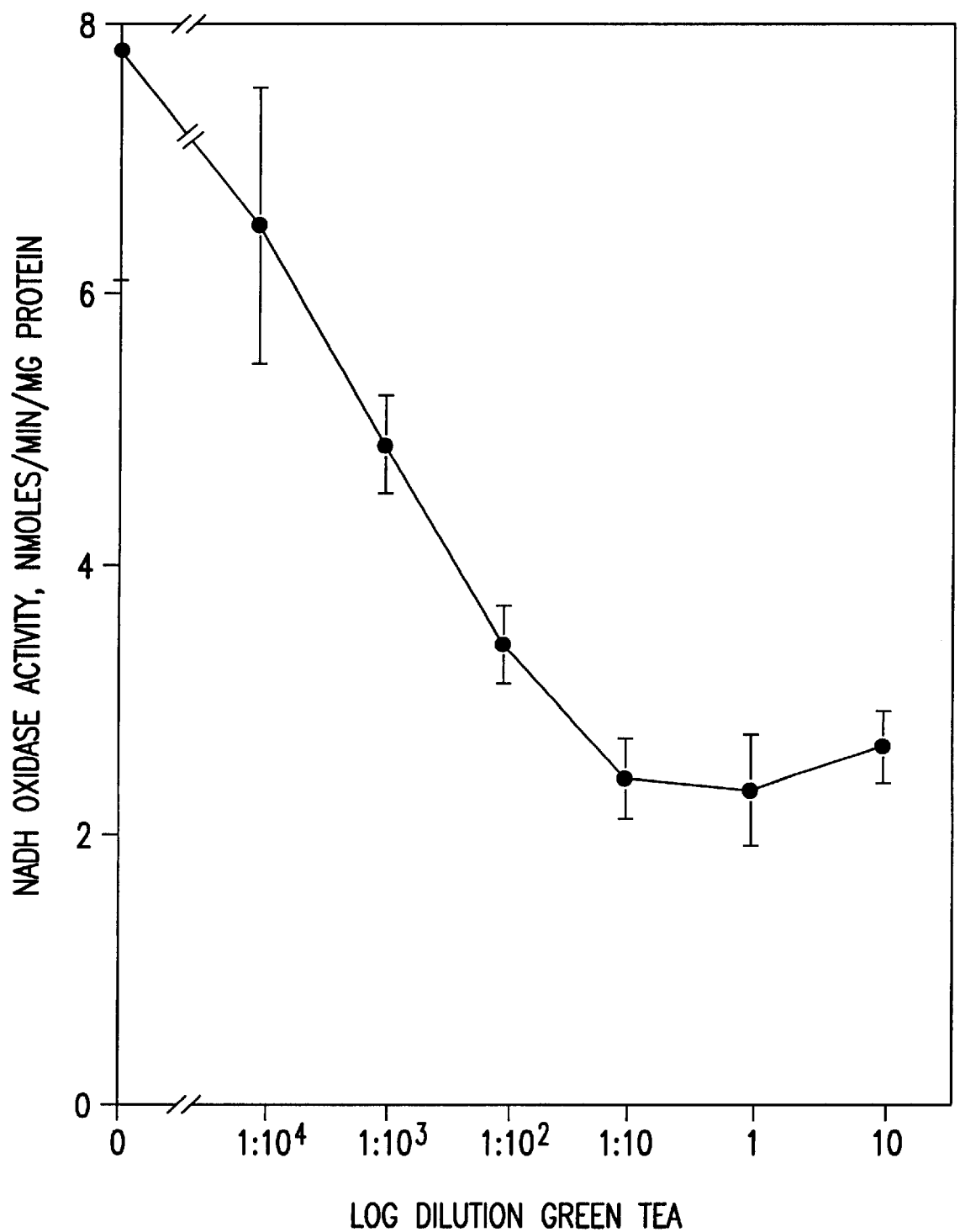

FIG. 6. Inhibition of partially purified tNOX from HeLa cells by green tea infusions.

The $EC_{50}$ for inhibition of the enzymatic activity was at a tea dilution of about 1:1000. The preparations contained an activity resistant to inhibition as well so that the inhibition by the tea infusions was not complete and further inhibition by green tea was not observed above a dilution of about 1:10. Results are averages of duplicate determinations in each of three separate experiments (n =6) ±standard deviations among experiments (n=3).

Figure 7:
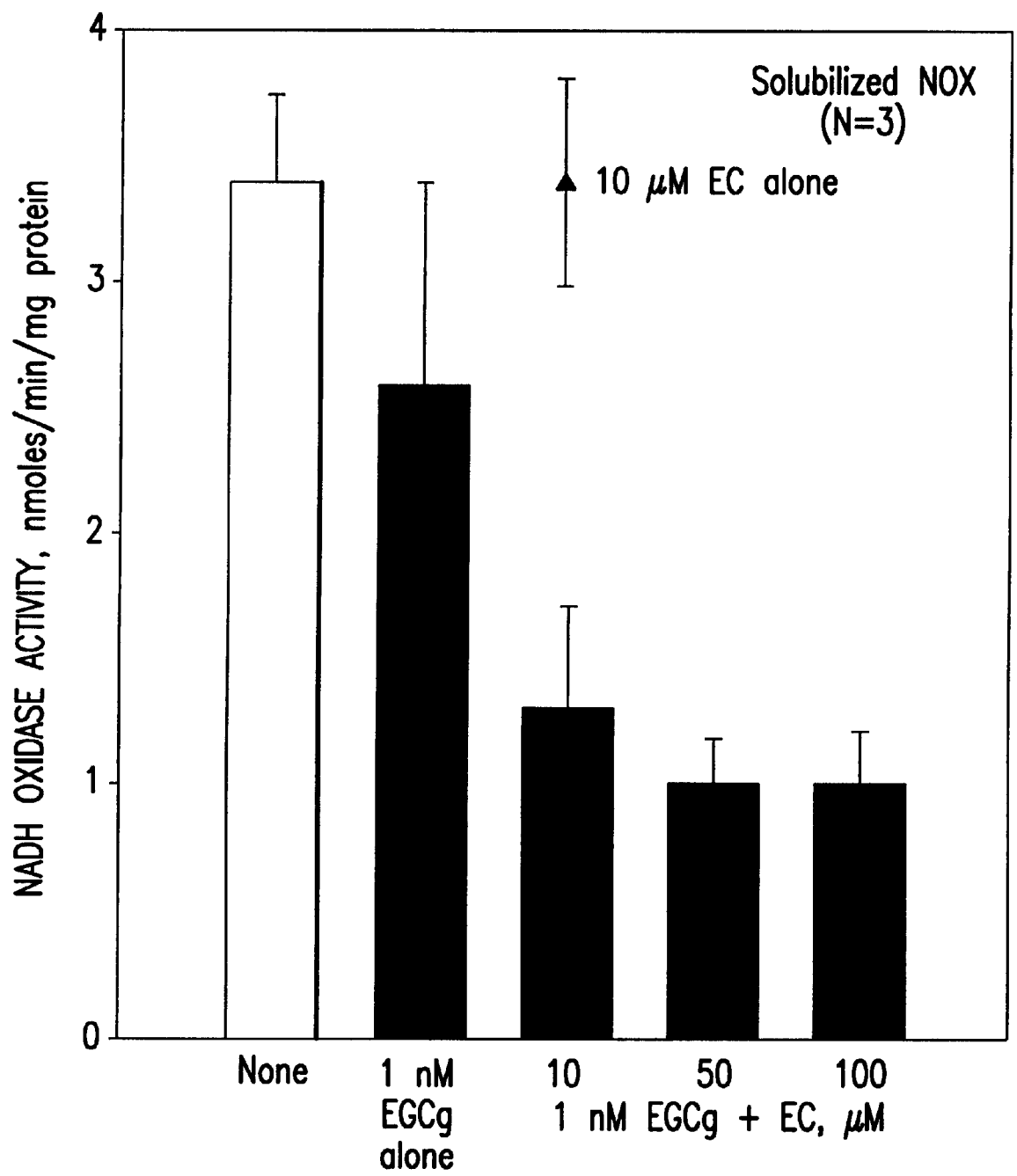

FIG. 7. Response of the NADH oxidase activity solubilized and partially purified as described from plasma membrane vesicles of HeLa cells to 1 nM (−)-epigallocatechin gallate (EGCg) alone and in combination with (−)-epicatechin (EC) at 10, 50 and 100 μM (del Castillo et al, 1998, Arch.

Biochem. Biophys. 358:125–140). Values are from duplicate determinations from each of three different experiments ± standard deviations. HeLa cells contain NOX activities containing both a drug-susceptible component (tNOX, 40 to 60% of the total) and a drug-resistant component (CNOX, 40 to 60%) of the total. The effect of EC in the presence of 1 nM EGCg alone is to inhibit completely the tNOX component without an effect on CNOX activity.

Figure 8:
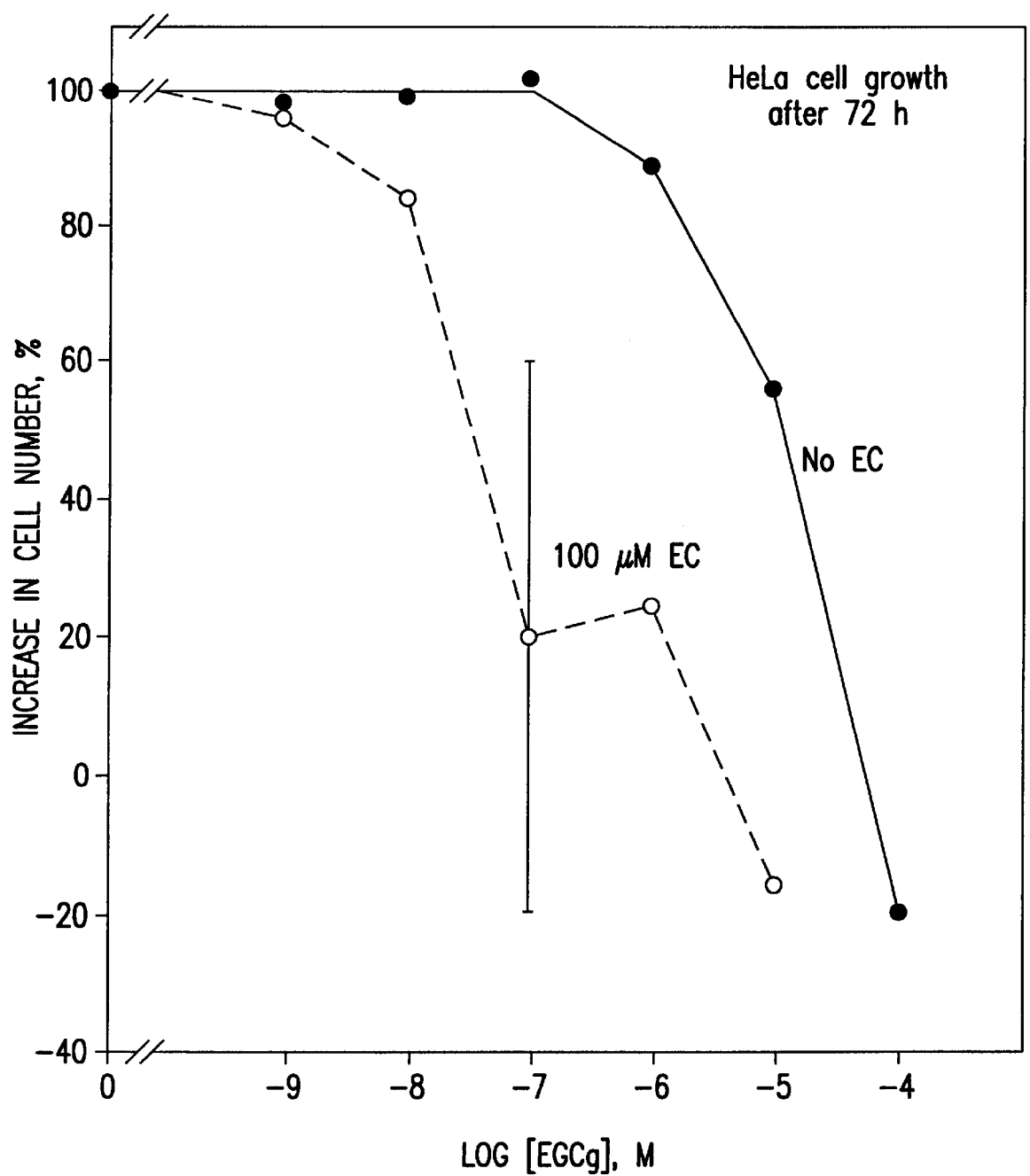

FIG. 8. Dose response of the growth of HeLa cells after 72 h to (−)-epigallocatechin (EGCg) in the absence or presence of 100 μM (−)-epicatechin (EC). Values are from duplicate determinations from single experiments except for $10^{-7}$ M EGCg which is the average of duplicate determinations from 3 experiments ± standard deviations.

Figure 9:
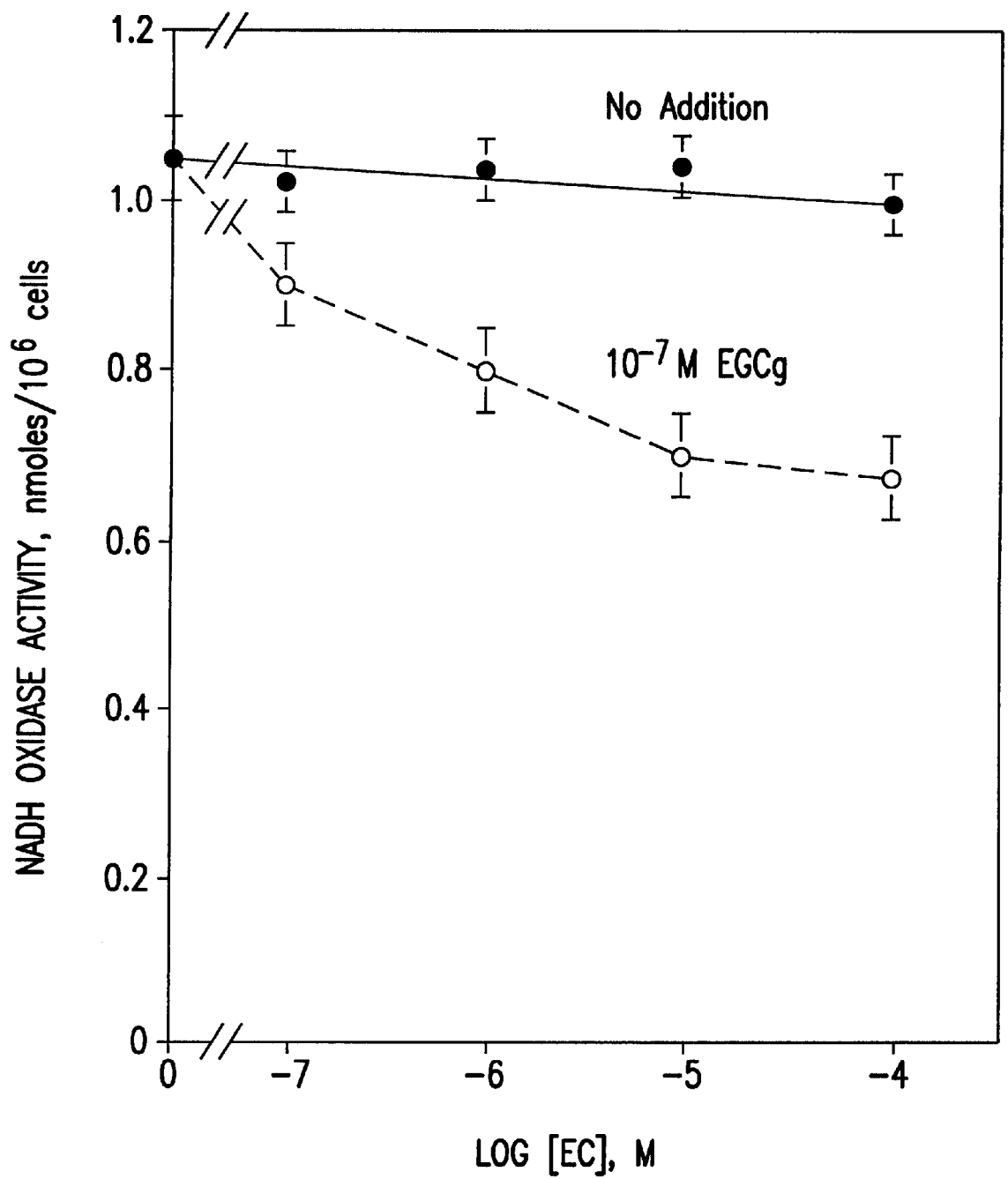

FIG. 9. Response of the NADH oxidase of 4T1 mouse mammary cells to (−)-epicatechin (EC) alone (upper curve, solid symbols) or in the presence of $10^{-7}$ M (−)-epigallocatechin gallate (EGCg) (lower curve, open symbols, dashed line). The tNOX activity (see FIG. 12) was completely inhibited by $10^{-4}$ M EC in the presence of 0.1 μM EGCg without effect on CNOX activity. Values are averages of 3 experiments ± standard deviations.

Figure 10:
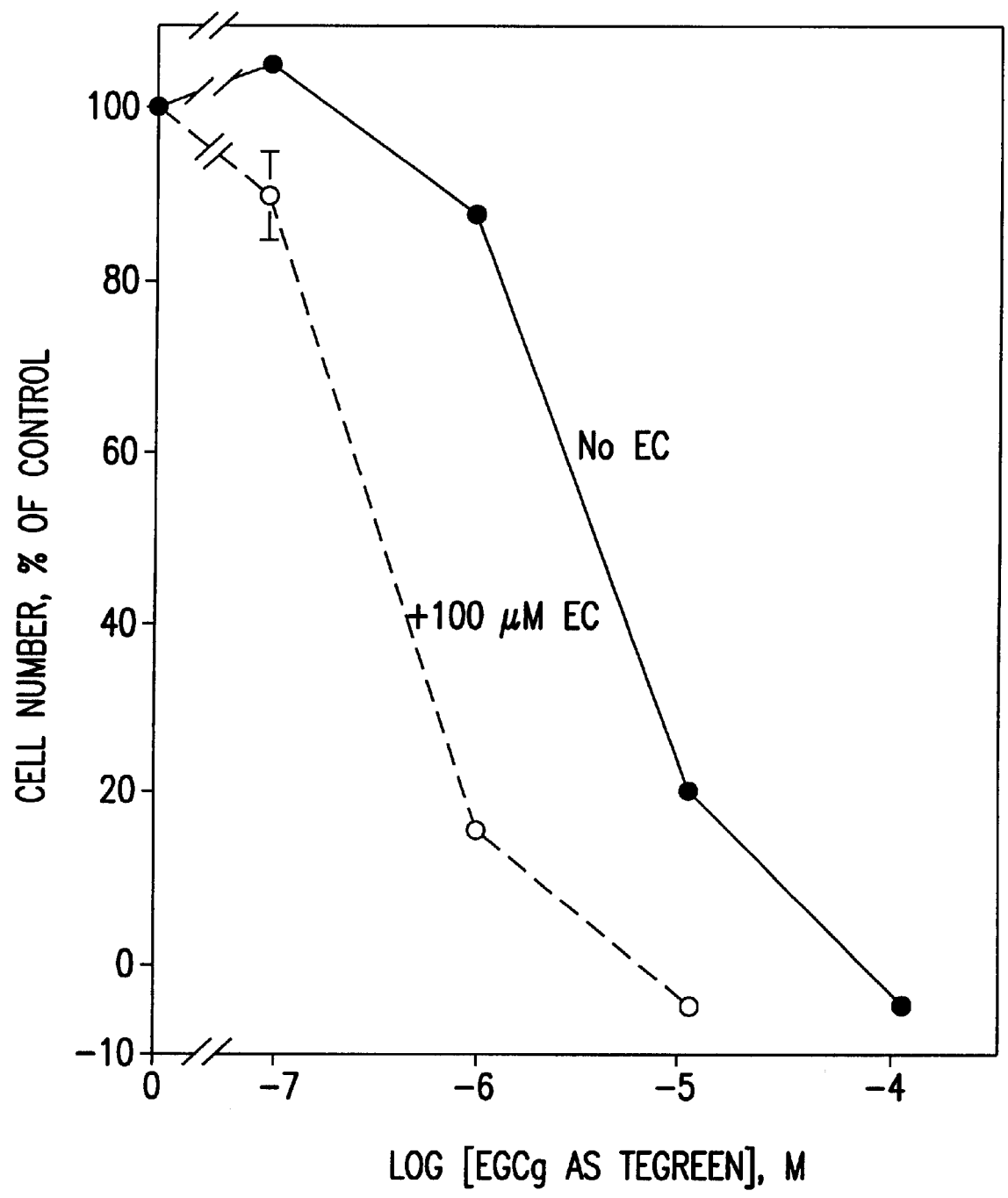

FIG. 10. Dose response of the growth of 4T1 cells after 72 h to (−)-epigallocatechin gallate (EGCg) provided in combination with other tea catechins as Tegreen™ in the absence or presence of 100 μM (−)-epicatechin (EC). Values are from duplicate determinations from single experiments except for $10^{-7}$ M EGCg which is the average of duplicate determinations from 3 experiments ± standard deviations.

Figure 11:
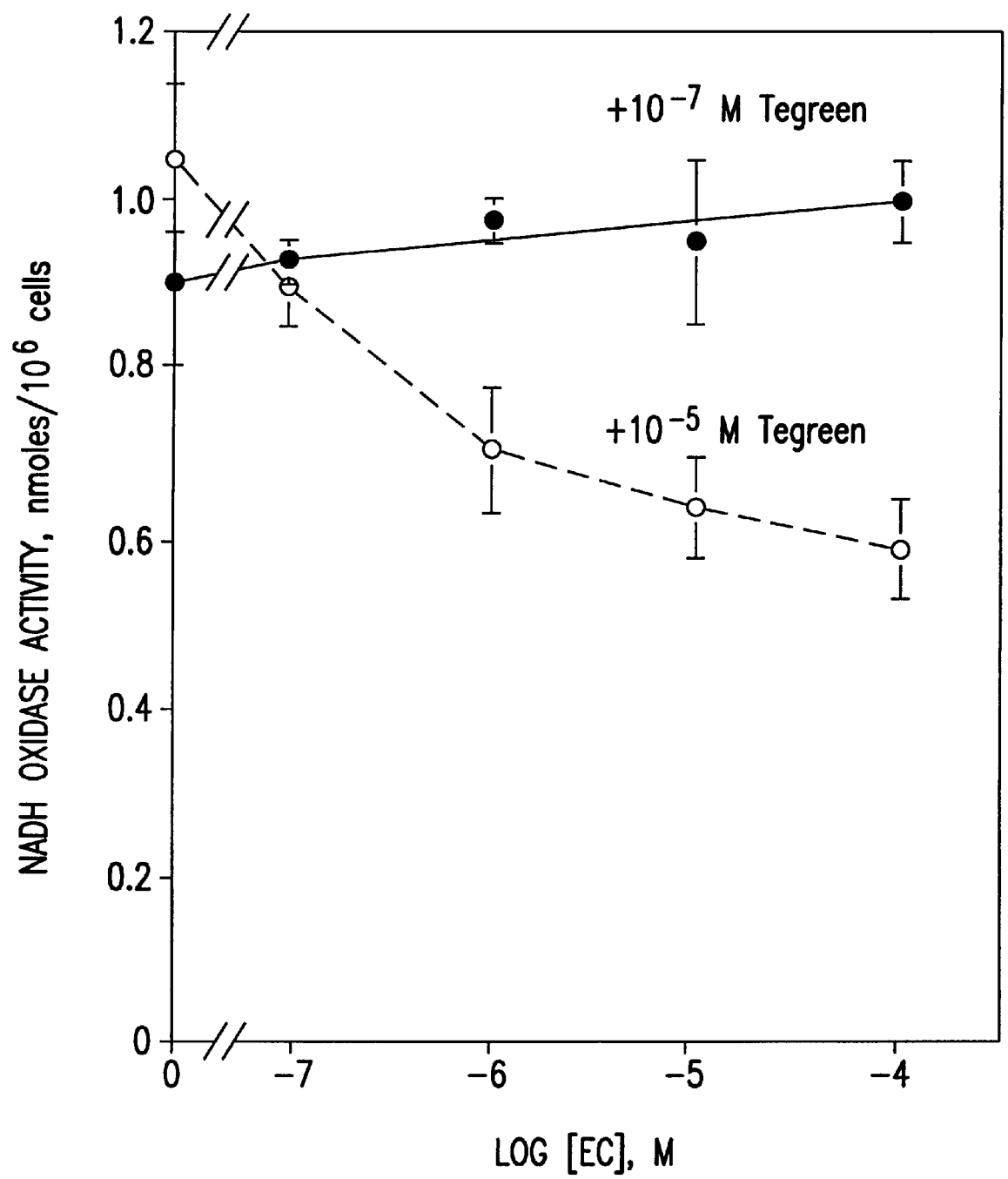

FIG. 11. Response of the NADH oxidase of 4T1 mouse mammary cells to (−)-epicatechin (EC) in the presence of $10^{-7}$ M Tegreen™ (upper curve, solid symbols) or $10^{-5}$ M Tegreen™ (lower curve, open symbols, dashed line). The tNOX activity (see FIG. 12) was completely inhibited by $10^{-4}$ M EC in the presence of 0.1 μM EGCg without effect on CNOX activity. Values are averages of 3 experiments ± standard deviations.

Figure 12:
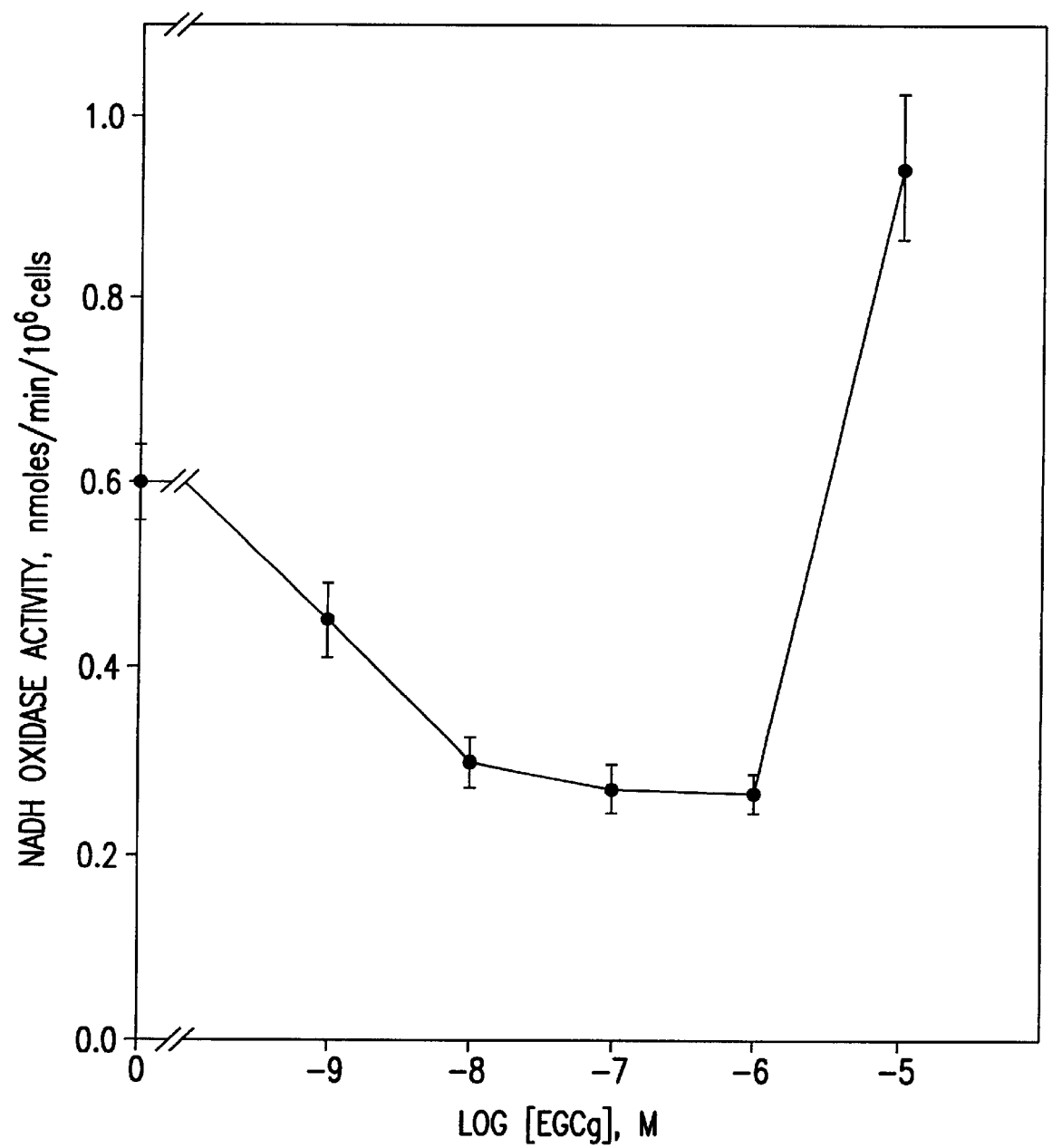

FIG. 12. Response of the NADH oxidase of HeLa S cells to (−)-epigallocatechin gallate (EGCg) alone. The tNOX activity was maximally inhibited by 0.1 μM EGCg without effect on CNOX activity. Values are averages of 3 experiments ± standard deviations.

Figure 13:
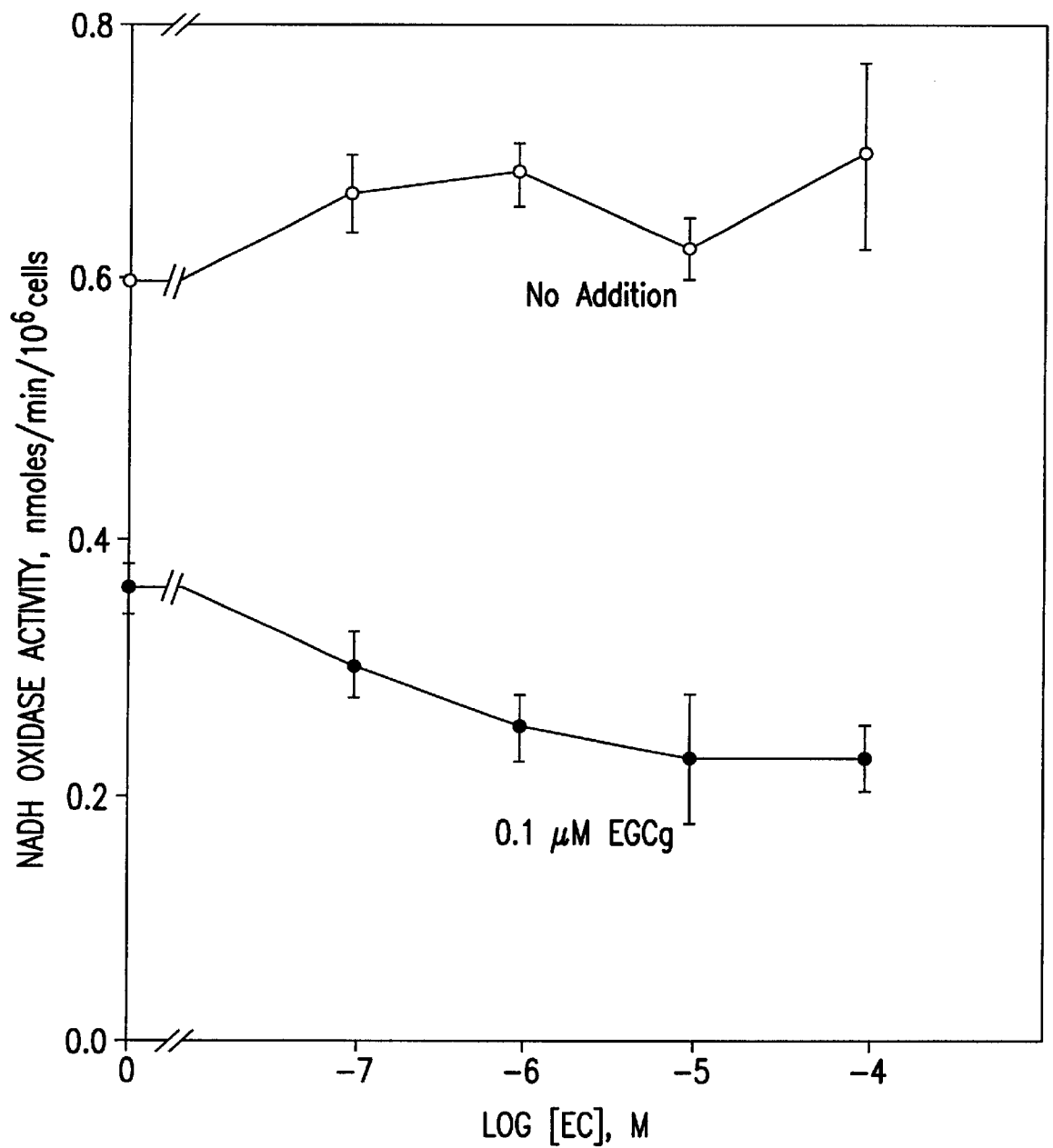

FIG. 13. Response of the NADH oxidase of HeLa S cells to (−)-epicatechin (EC) alone (upper curve, solid symbols) or in the presence of $10^{-7}$ M epigallocatechin gallate (EGCg) (lower curve, open symbols, dashed line). The tNOX activity was completely inhibited by $10^{-4}$ M EC in the presence of 0.1 μM EGCg without effect on CNOX activity. Values are averages of 3 experiments ± standard deviations.

Figure 14:
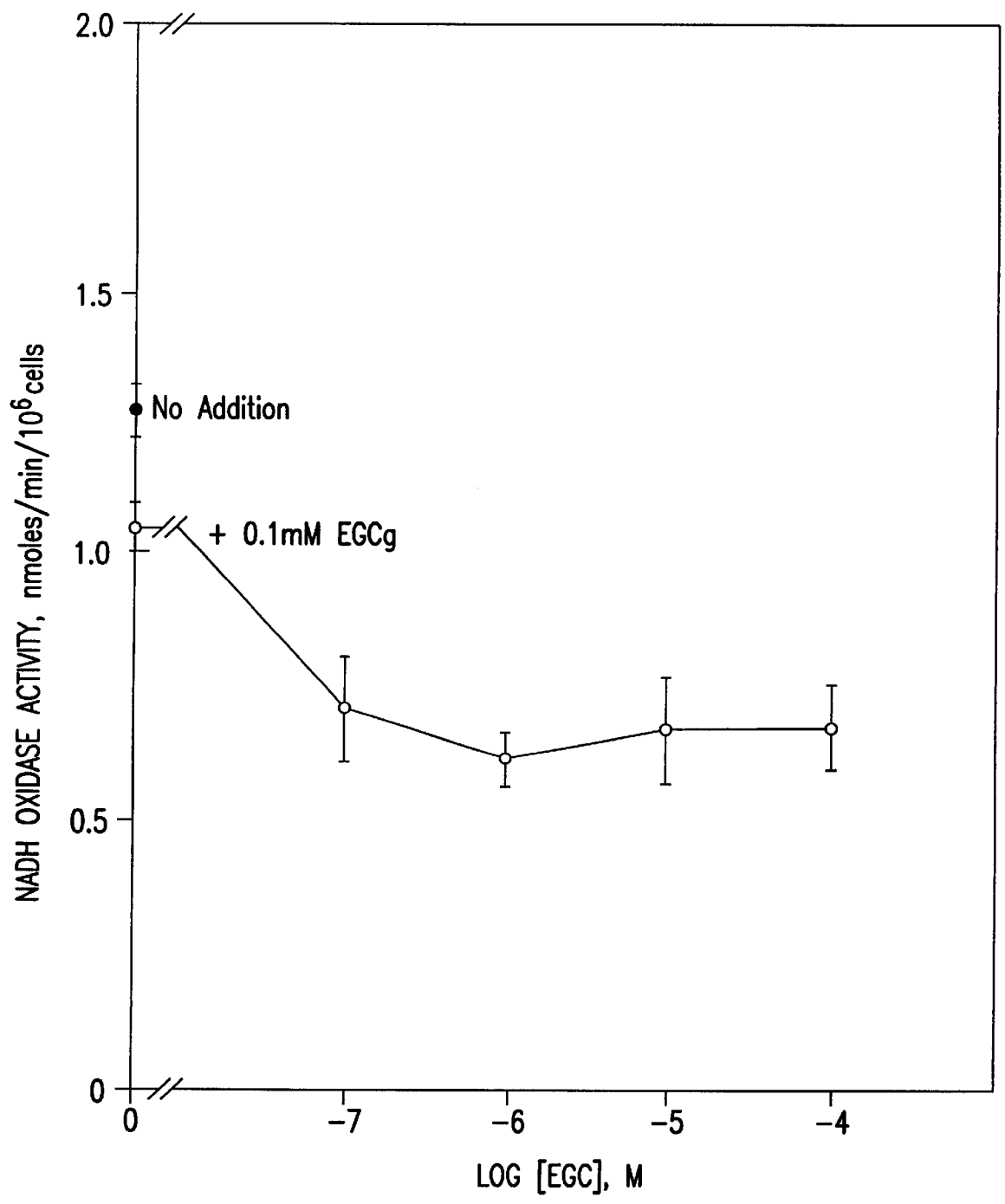

FIG. 14. Response of the NADH oxidase of 4T1 mouse mammary cells to varying concentrations of (−)-epicatechin gallate (ECG) alone or in the presence of $10^{-7}$ M (−)-epigallocatechin gallate (EGCg). The tNOX activity was completely inhibited by $10^{-6}$ M EC in the presence of 0.1 μM EGCg without effect on CNOX activity. Values are averages of duplicate determinations from 2 experiments ± mean average deviations between the two experiments.

Figure 15:
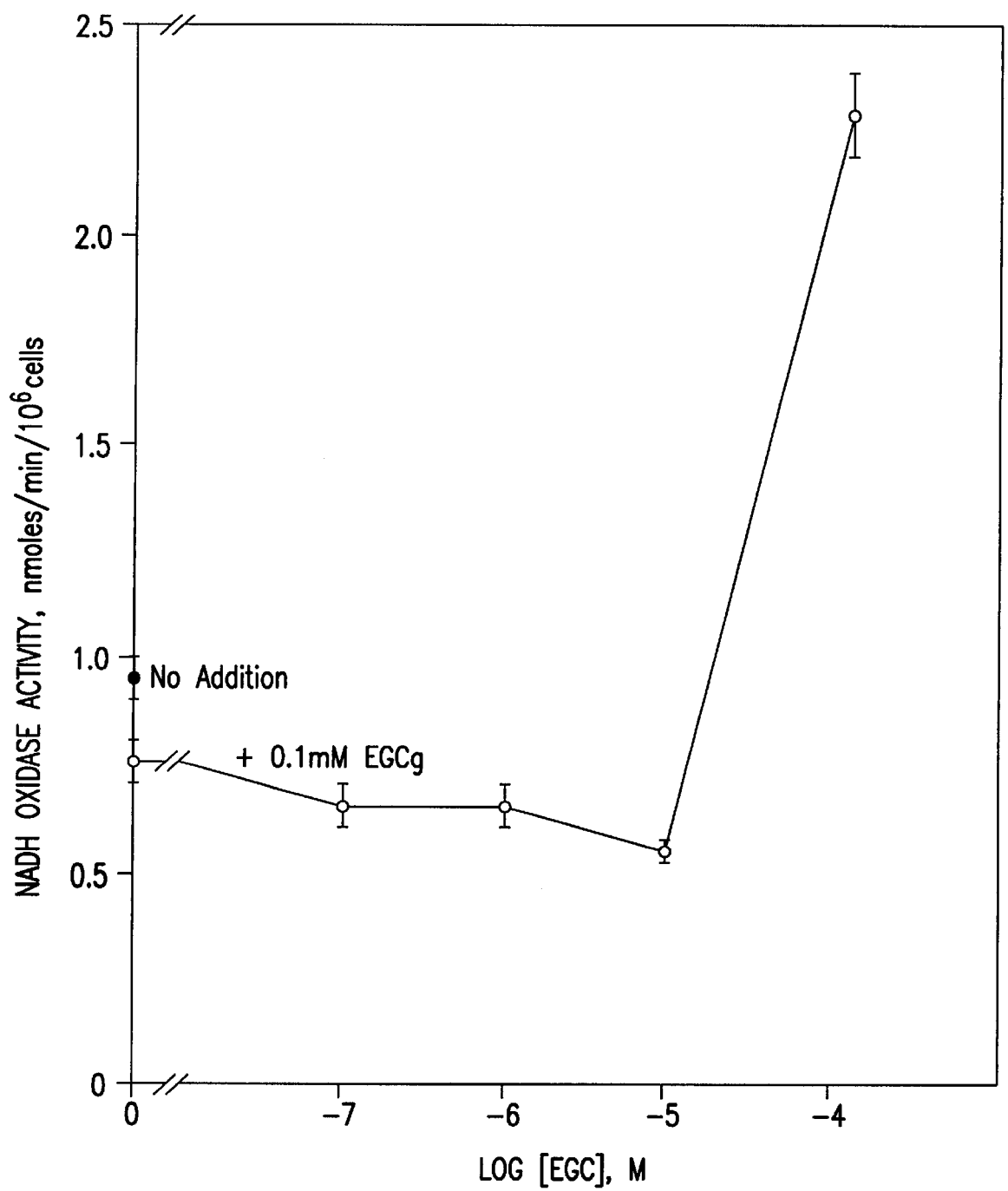

FIG. 15. Response of the NADH oxidase of 4T1 mouse mammary cells to varying concentrations of (−)-epigallocatechin (EGC) in the presence of $10^{-7}$ M (−)-epigallocatechin gallate (EGCg). The tNOX activity was completely inhibited by $10^{-5}$ M EC in the presence of 0.1 μM EGCg without effect on CNOX activity. Values are averages of duplicate determinations from 2 experiments ± mean average deviations between the two experiments.

Figure 16:
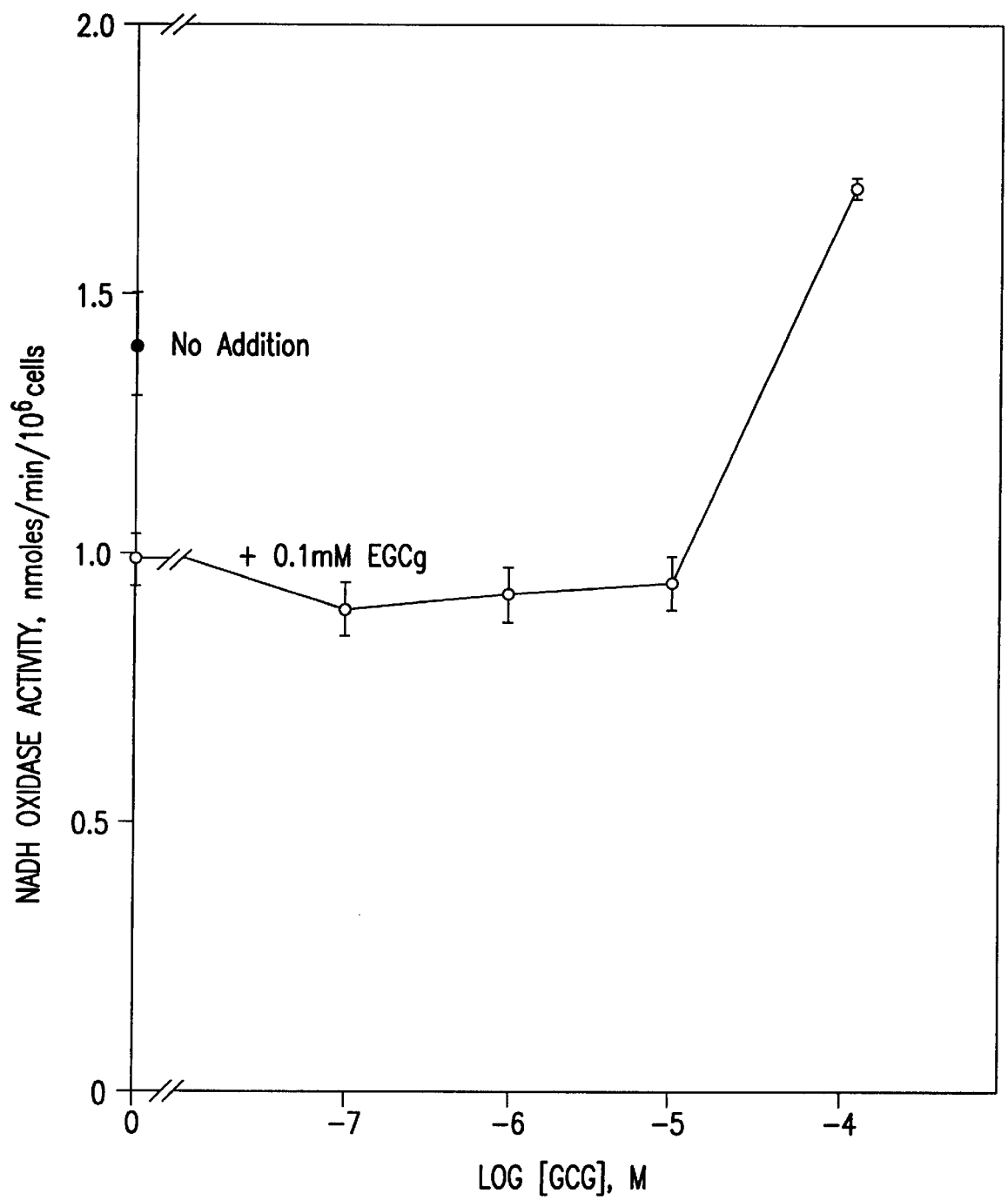

FIG. 16. Response of the NADH oxidase of 4T1 mouse mammary cells to varying concentrations of (−)-epigallocatechin gallate (GCG) in the presence of $10^{-7}$ M (−)-epigallocatechin gallate (EGCg). The NOX activity was less affected by GCG in the presence of 0.1 mM EGCg than for EC (Table 5), ECG (FIG. 14) or EGC (FIG. 15). Values are averages of duplicate determinations from 2 experiments ± standard deviations among the three experiments.

Figure 17:
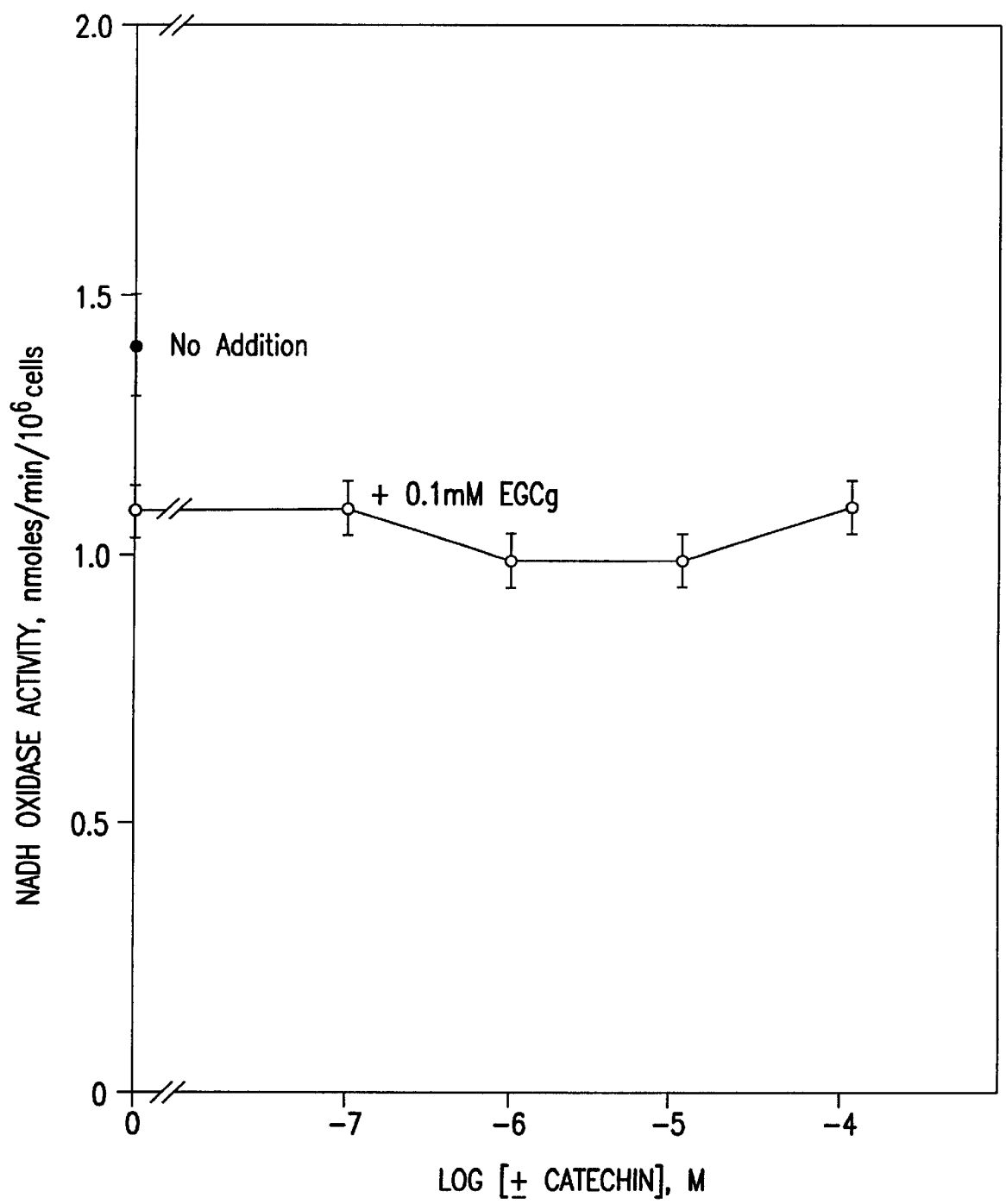

FIG. 17. Response of the NADH oxidase of 4T1 mouse mammary cells to varying concentrations of ± catechin in the presence of $10^{-7}$ M (−)-epigallocatechin gallate (EGCg). The NOX activity was little affected by ± catechin either in the presence or absence (not shown) of 0.1 μM EGCg. Values are averages of duplicate determinations from 3 experiments ± standard deviations among the three experiments.

Figure 18:
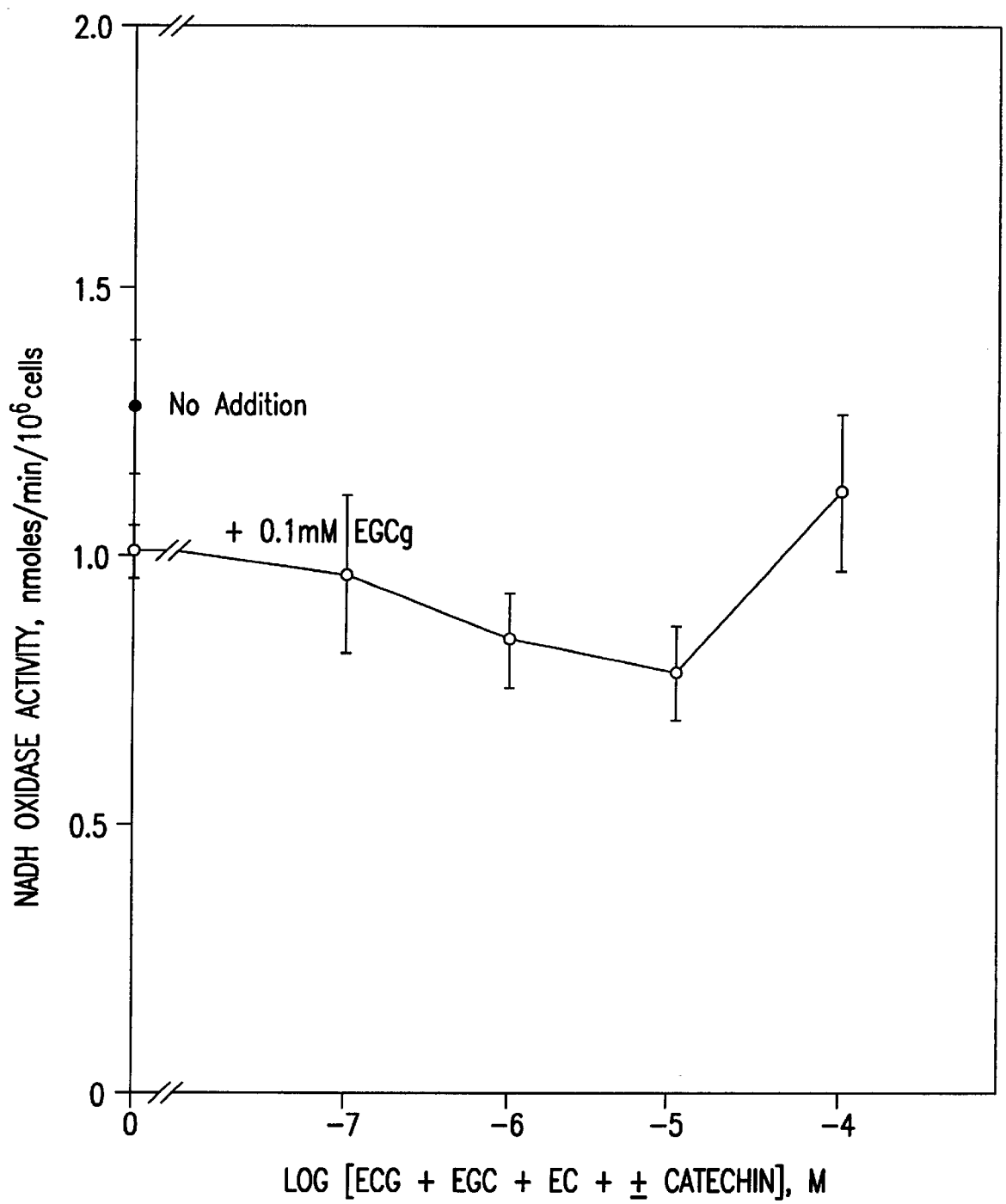

FIG. 18. Response of the NADH oxidase of 4T1 mouse mammary cells to varying concentrations of a mixture of equal parts of ECG, EGC, EC and ± catechin in the presence of $10^{-7}$ M (−)-epigallocatechin gallate (EGCg). The NOX activity was completely inhibited by $10^{-5}$ to $10^{-6}$ M of the mixture in the presence of 0.1 μM EGCg without effect on CNOX activity. Values are averages of duplicate determinations from 3 experiments ± standard deviations among the three experiments.

Figure 19:
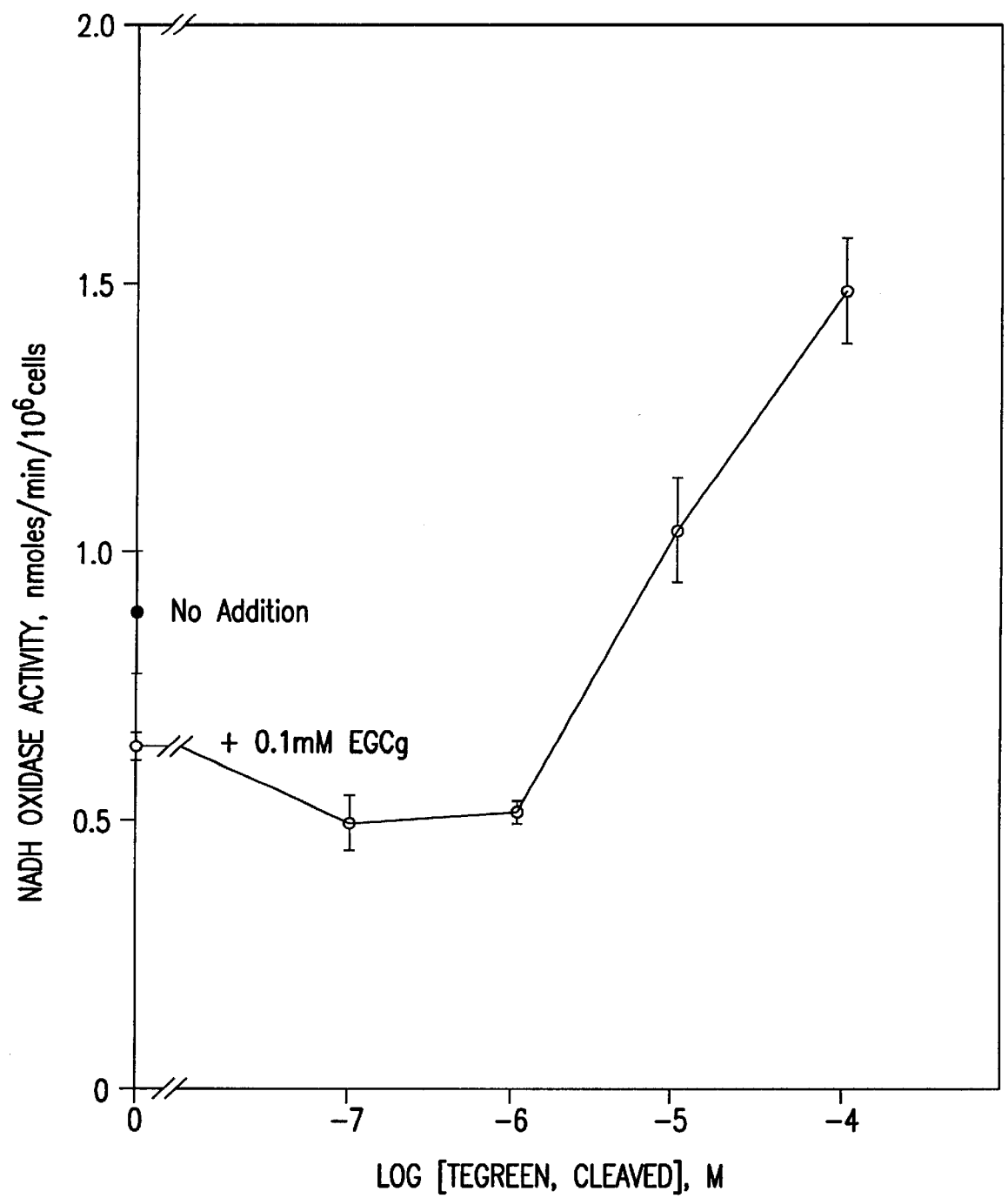

FIG. 19. Response of the NADH oxidase of 4T1 mouse mammary cells to varying concentrations of Tegreen™ a concentration equivalent to $10^{-7}$ EGCg treated with NaOH to cleave gallate esters. The hydrolyzate was tested in the presence of $10^{-7}$ M (−)-epigallocatechin gallate (EGCg). The base was neutralized to pH 7 with HCl and a control experiment with an equivalent amount of NaCl was carried out. The tNOX activity was completely inhibited by EGCg of Tegreen™ in the presence of 0.1 mM EGCg without effect on CNOX activity. Values are averages of duplicate determinations from 2 experiments ± mean average deviations between the two experiments.

Figure 20:
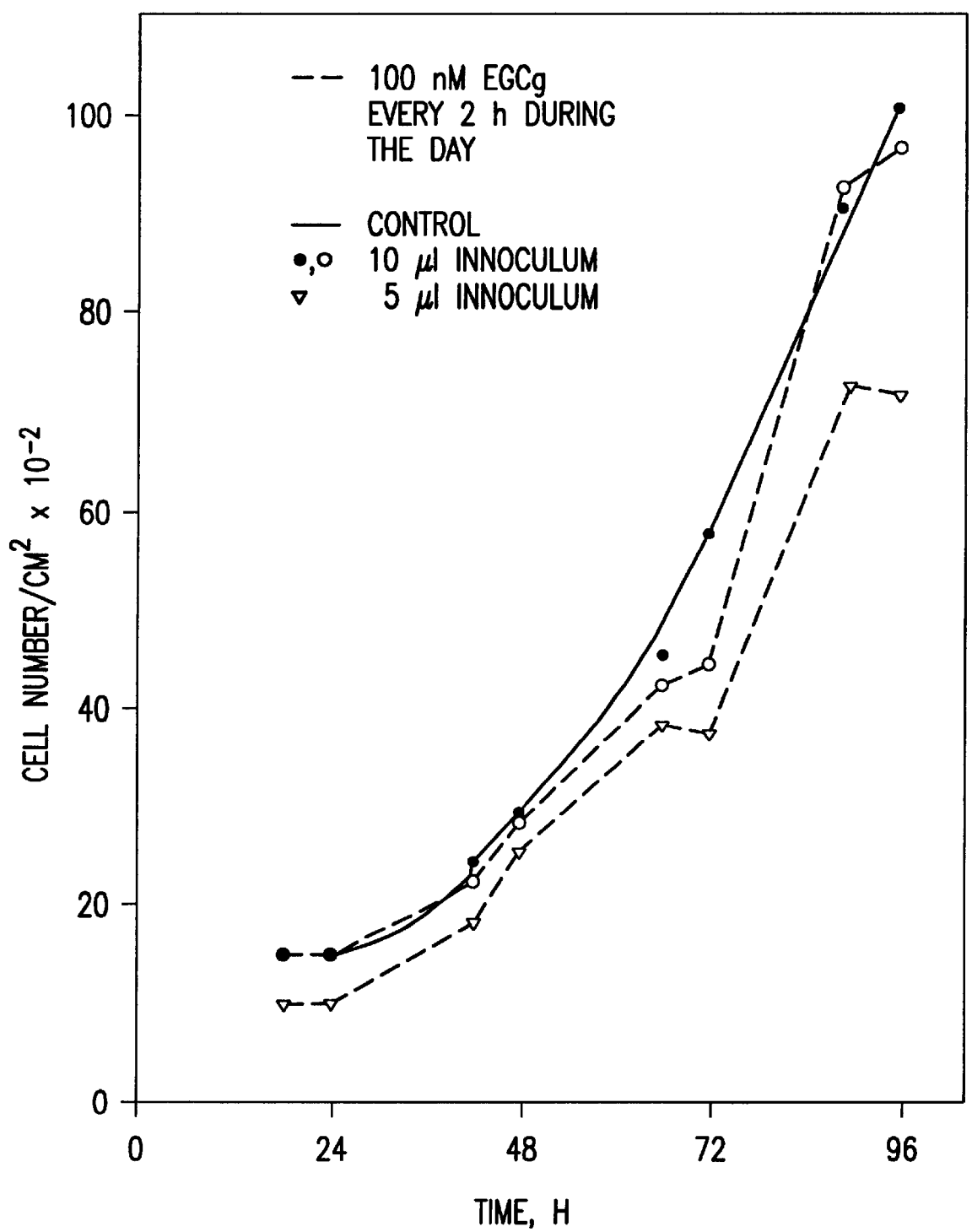

FIG. 20. Growth of HeLa cells (increase in cell number) with time of culture. No addition (solid symbols, solid line). EGCg (100 nM) was added every 2 hours during the day (8:00 a.m. until 5:00 p.m.) (open symbols, dashed lines). Two different levels of inoculum 10 μl (circles) or 5 μl (triangles) were compared.

Figure 21:
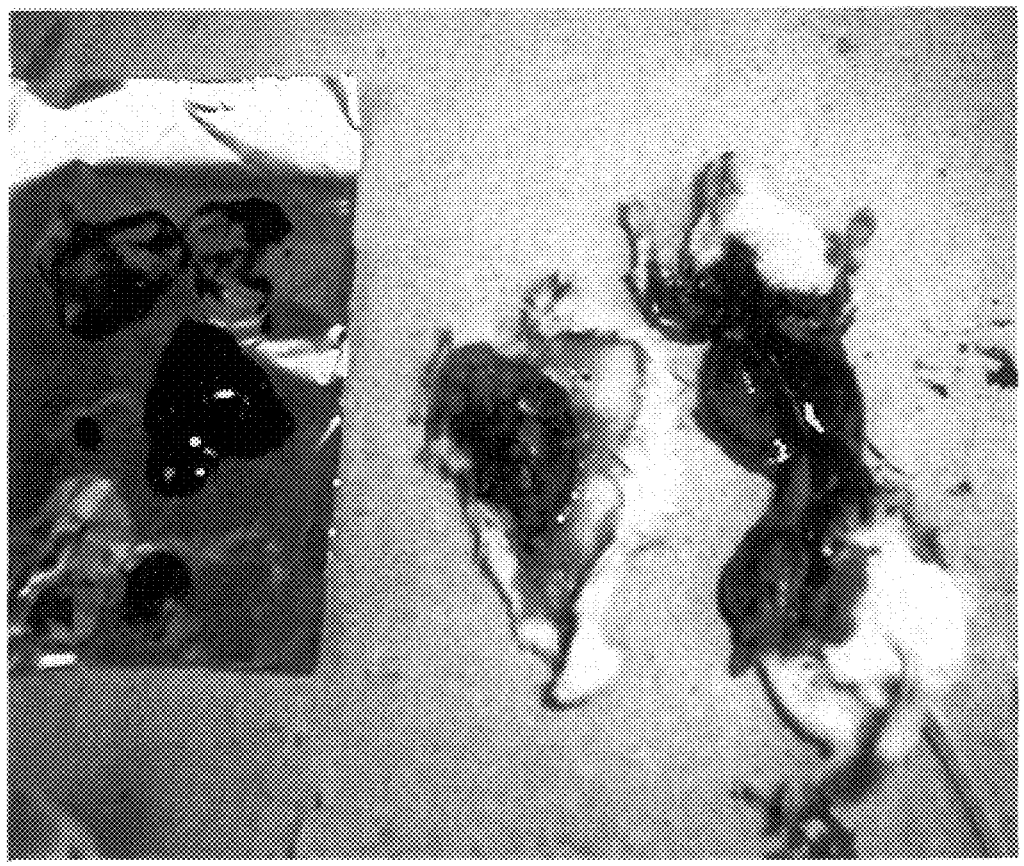

FIG. 21. Effect of sustained release formulation of Tegreen™ on tumor growth in a Balb C mouse bearing a transplantable 4T-1 mammary adenocarcinoma. A tumor mass lying on an adhering sheet of mouse skin is shown in the center. The tumor was treated with 100 μl of a suspension of 2.3 mg/ml of the sustained release formulation of Tegreen™. On the left are the lung, liver, and lymph nodes, as controls to indicate that metastasis to these organs had not occured. Wherever a small granule of the sustained release material was located in the tumor mass, the cells were killed for several mm around the particle.

5. DETAILED DESCRIPTION OF THE INVENTION

The invention encompasses sustained release formulations comprising catechins, a group of polyphenols found in green tea, which are used as therapeutic compounds for the treatment of cancer or as a dietary supplement that offers white blood cell protection and maintains healthy blood levels, all of which suggests that the catechins play a role in the prevention of cancer. The sustained release compositions optimally maintain circulating levels of said composition in the body at a certain threshold level over an extended time period. Specific therapeutic regimens, pharmaceutical compositions, and kits are also provided by the invention.

In one embodiment, the invention described herein comprises the administration of a therapeutically effective amount of catechins in a sustained release formulation to a mammal in need of such therapy. In a preferred embodiment, the mammal is a human. In another embodiment, the invention further encompasses the use of combination therapy to treat cancer.

In a specific embodiment, the catechins comprise epigallocatechin gallate (EGCg), epicatechin gallate (ECG), epigallocatechin (EGC), and epicatechin (EC) or a combination thereof, optionally in combination with other polyphenols.

The disclosure is based, in part, on the discovery that epigallocatechin gallate (EGCg), alone and in combination with other catechins and other anti-cancer therapeutic agents, inhibits the activity of a cancer-specific protein, an isoform of NADH oxidase specific to cancer cells (tNOX). The inhibition of tNOX results in the inhibition of cell growth, and ultimately, apoptosis of the cancer cell, whereas normal cells (which lack tNOX but instead express the isoform CNOX) are less affected. Thus, the invention provides a potent therapeutic effect without or while reducing the adverse effects on normal, healthy cells.

Significantly the effect of the catechins such as EGCg is reversible, i.e., if the EGCg is removed, cancer cells resume normal rates of growth. Other discoveries include: (1) EGCg is rapidly cleared from culture media and metabolized, (2) cancer cells must be inhibited from growing for 48 to 72 hours before EGCg-induced apoptosis occurs, and (3) when cancer cells are challenged with $10^{-7}$ M EGCg every two hours during the day, their growth is inhibited, but during the night normal cell growth resumes in the absence of further EGCg addition. Thus, the invention is directed to the administration of sustained release formulations so that a constant level of the catechins is maintained.

Particular compositions of the invention and their uses are described in the sections and subsections which follow.

5.1. Catechin Formulations
5.1.1. Percentages of the Varying Polyphenols The invention comprises formulations (e.g., specific combination of catechins and specific levels) of green tea polyphenols, in particular, catechins, for the prevention and/or treatment of cancer. The typical percentage of the individual catechins in green tea extracts is 10–15% EGCg, 2–3% ECG, 2% EC, and 2–3% EGC (Suganuma et al., 1999, Can. Res. 59:44–47).

In contrast, in one embodiment of the present invention, EGCg comprises at least 30% of the total catechins. In a preferred embodiment, EGCg comprises about 35% to about 45% of the total catechins. In a more preferred embodiment, EGCg comprises about 40% of the total catechins.

Although the invention encompasses the use of a composition containing certain levels of EGCg alone, it is preferred that EGCg be used in combination with other catechins, more specifically, those described infra.

In another embodiment, EGCg comprises at least 30% of the total catechins and ECG comprises at least 5% of the total catechins. In a preferred embodiment, EGCg comprises about 35% to about 45% of the total catechins and ECG comprises about 10% to about 20% of the total catechins. In a more preferred embodiment, EGCg comprises about 40% of the total catechins and ECG comprises about 15% of the total catechins.

In another embodiment, EGCg comprises at least 30% of the total catechins and EC comprises at least 3% of the total catechins. In a preferred embodiment, EGCg comprises about 35% to about 45% of the total catechins and EC comprises about 3% to about 15% of the total catechins. In a more preferred embodiment, EGCg comprises about 40% of the total catechins and EC comprises about 7% of the total catechins.

In an additional embodiment, EGCg comprises at least 0.01% of the total catechins and EC comprises an amount which is at least 100 fold greater than the EGCg content of the total catechins. The total catechins may or may not include the additional catechins such as those described above, e.g., ECG, EGC, C, etc. In a preferred embodiment, EC comprises an amount which is at least 100 fold greater than the EGCg content. In another preferred embodiment, EC comprises an amount which is at least 1000 fold greater than the EGCg content.

In another embodiment, EGCg comprises a negligible amount of the catechin formulation.

In an additional embodiment, EGCg comprises at least 30% of the total catechins and EGC comprises at least 1% of the total catechins. In a preferred embodiment, EGCg comprises about 35% to about 45% of the total catechins and EGC comprises about 2% to about 5% of the total catechins. In a more preferred embodiment, EGCg comprises about 40% of the total catechins and EGC comprises about 3% of the total catechins.

In an additional embodiment, EGCg comprises at least 30% of the total catechins, EC comprises at least 3% of the total catechins, and ECG comprises at least 5% of the total catechins. In a preferred embodiment, EGCg comprises about 35% to about 45% of the total catechins, EC comprises about 3% to about 15% of the total catechins, and ECG comprises about 10% to about 20% of the total catechins. In a more preferred embodiment, EGCg comprises about 40% of the total catechins, EC comprises about 7% of the total catechins and ECG comprises about 15% of the total catechins.

In yet another embodiment, EGCg comprises at least 30% of the total catechins, EC comprises at least 3% of the total catechins, and EGC comprises at least 1% of the total catechins. In a preferred embodiment, EGCg comprises about 35% to about 45% of the total catechins, EC comprises about 3% to about 15% of the total catechins, and EGC comprises about 2% to about 5% of the total catechins. In a more preferred embodiment, EGCg comprises about 40% of the total catechins, EC comprises about 7% of the total catechins, and EGC comprises about 3% of the total catechins.

In yet another embodiment, EGCg comprises at least 30% of the total catechins, EC comprises at least 3% of the total catechins, ECG comprises at least 5% of the total catechins, and EGC comprises at least 1% of the total catechins. In a preferred embodiment, EGCg comprises about 35% to about 45% of the total catechins, EC comprises about 5% to about 15% of the total catechins, ECG comprises about 10% to about 20% of the total catechins, and EGC comprises 2% to about 5% of the total catechins. In a more preferred embodiment, EGCg comprises about 40% of the total catechins, EC comprises about 7% of the total catechins. ECG comprises about 15% of the total catechins, and EGC comprises about 3% of the total catechins.

In yet another embodiment, EGCg comprises at least 30% of the total catechins, EC comprises at least 3% of the total catechins, ECG comprises at least 5% of the total catechins, EGC comprises at least 1% of the total catechins, and C comprises at least 5% of the total catechins. In a preferred embodiment, EGCg comprises about 35% to about 45% of the total catechins, EC comprises about 5% to about 15% of the total catechins, ECG comprises about 10% to about 20% of the total catechins, EGC comprises 2% to about 5% of the total catechins, and C comprises about 10% to about 20% of the total catechins. In a more preferred embodiment, EGCg comprises about 40% of the total catechins, EC comprises about 7% of the total catechins. ECG comprises about 15% of the total catechins, EGC comprises about 3% of the total catechins, and C comprises about 15% of the total catechins.

The level of caffeine is generally less than about 5% and is preferably less than 0.5% of the polyphenols.

The invention comprises all pharmaceutically acceptable derivatives of the catechins listed supra, and their combinations thereof.

5.1.2. Sustained Release Formulation

The invention comprises a mixture of catechins, including but not limited to the percentages of the polyphenols described supra, formulated as sustained release compositions. In a specific embodiment, the invention comprises a mixture of catechins which when administered to a human results in circulating levels of EGCg is maintained between $10^{-9}$ and $10^{-4}$ M. In a preferred embodiment for the prevention of cancer, the circulating levels of all catechins in the catechin mixture is maintained up to $10^{-7}$ M. In a preferred embodiment for the treatment of cancer, the circulating levels of all catechins in the catechin mixture is maintained up to $10^{-7}$ M. The levels are either circulating in the patient systemically, or in a preferred embodiment, localized to the tumor, and in a most preferred embodiment, localized to the cell surface of the cancer cells.

It is understood that the catechin levels are maintained over a certain period of time as is desired and can be easily determined by one of skill in the art using this disclosure and available pharmaceutical compendia. In a preferred embodiment, the invention includes a unique feature of administration comprising a sustained release formulation so a constant level of EGCg is maintained between $10^{-8}$ and $10^{-6}$ M between 48 to 96 hours in the sera.

Such sustained and/or timed release formulations may be made by sustained release means or delivery devices that are well known to those of ordinary skill in the art, such as those described in U.S. Pat. Nos.: 3,845,770, 3,916,899, 3,536,809, 3,598,123, 4,008,719, 4,710,384, 5,674,533, 5,059,595, 5,591,767, 5,120,548, 5,073,543, 5,639,476, 5,354,556, and 5,733,566, the disclosures of which are each incorporated herein by reference. These pharmaceutical compositions can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

In a highly preferred embodiment, the sustained release formulation contains active ingredients such as, but not limited to, microcrystalline cellulose, maltodextrine, ethylcellulose, and magnesium stearate. In yet another highly preferred embodiment, the formulation is synthesized with a CapsuDar® SR (Biodar, Yavne, Israel) microencapsulation which consists of the active ingredients microcrystalline cellulose, maltodextrine, ethylcellulose, and magnesium stearate.

As described above, all known methods for encapsulation which are compatible with the properties of tea catechins are compassed by this invention. The sustained release formulation is encapsulated by coating particles or granules of the pharmaceutical composition of the invention with varying thicknesses of slowly soluble polymers or by microencapsulation. In a preferred embodiment, the sustained release formulation is encapsulated with a coating material of varying thickness (e.g., about 1 micron to 200 microns) that allows the dissolution of the pharmaceutical composition about 48 hours to about 72 hours after administration to a mammal. In another embodiment, the coating material is a food approved additive. In yet another embodiment, the coating material is sold under the trademark Eudragit RS or RL (Rohm Pharma, Germany).

In another embodiment, the sustained release formulation is a matrix dissolution device, which is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, have a relatively high percentage of plasticizer in the coating in order to permit sufficient flexibility to prevent substantial breakage during compression. The specific amount of plasticizer varies depending on the nature of the coating and the particular plasticizer used. The amount may be readily determined empirically by testing the release characteristics of the tablets formed. If the medicament is being released too quickly, then more plasticizer is used. Release characteristics are also a function of the thickness of the coating. When substantial amounts of plasticizer are used, the sustained released capacity of the coating diminishes. Thus, the thickness of the coating may be increased slightly to make up for an increase in the amount of plasticizer. Generally, the plasticizer in such an embodiment will be present in an amount of about 15 to 30 percent of the sustained release material in the coating, preferably 20 to 25 percent and the amount of coating will be from 10 to 25 percent of the weight of active material, preferably 15 to 20 percent. Any conventional pharmaceutically acceptable plasticizer may be incorporated into the coating.

5.2. Target Cancers

Cancers that can be treated by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic Iymphocytic leukemia); and polycythemia vera, lymphoma (Hodgkin's disease and non-Hodgkin's disease), multiple myeloma, Waldenstrom's macroglobulinemia, and heavy chain disease.

In a preferred embodiment, the cancer is one where circulating levels of tNOX are present in the sera of patients suffering from said cancer, e.g., rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma, see e.g., U.S. Pat. No. 5,605,810, which is incorporated by reference in its entirety.

In a preferred embodiment, the patient already has cancer and is undergoing treatment for said cancer. In a specific embodiment, the patient already has cancer but no metastasis. i.e., secondary cancer. In another specific embodiment, the patient already has cancer plus a metastatic cancer. In another specific embodiment, the patient having a cancer is immunosuppressed by reason of having undergone anti-cancer therapy (e.g., chemotherapy or radiation) prior to administration of the catechin complexes of the invention.

In another specific embodiment, the cancer is a tumor. In a preferred embodiment, the tumor is a tumor of epithelial tissue, lymphoid tissue, connective tissue, bone, or central nervous system.

5.3. Combination Therapy

The invention encompasses the catechin formulations listed in Section 5.1 administered in combination with other therapeutic agents, such as anti-cancer drugs. The therapeutic agents include, but are not limited to adriamycin and adriamycin conjugates, mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouacil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof. The therapeutic agents which inhibit tNOX and cancer cell growth include adriamycin, bullatacin, simalikalactone D, and glaucarubolone has been demonstrated by the Inventors in U.S. Pat. No. 5,605,810, which is incorporated by reference in its entirety for all purposes.

The invention also embodies the catechin formulations, anti-cancer agents, and combinations thereof for the treatment of cancer patients undergoing chemotherapy and/or irradiation for a primary cancer. In a preferred embodiment, the catechin formulations, anti-cancer agents, and combinations thereof provides a method for treating the metastasized, i.e. secondary cancer, in said patients.

In another embodiment, the secondary agent administered, in addition to the catechin formulations, includes a monoclonal antibody directed against tNOX for combination therapy. A monoclonal antibody to the human tNOX protein isolated from the sera of cancer patients has already successfully been used in the expression cloning of tNOX from HeLa cells (Chueh et al., 1997, Arch. Biochem. Biophys. 342:38–44).

5.4. Pharmaceutical Compositions for Cancer Treatment

Catechin complexes of the invention may be formulated into pharmaceutical preparations for administration to mammals for treatment of cancer. In a preferred embodiment, the mammal is a human.

Compositions comprising a compound of the invention formulated in a compatible pharmaceutical carrier may be prepared, packaged, and labelled for treatment of the indicated cancer, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myclomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

5.5. Modes of Administration
5.5.1. Sustained Release Formulation

The catechins of the invention are formulated as a sustained and/or timed release formulation. Applicants provide a description of a response to the catechins which is reversible in cells (see Example 6, infra). Furthermore, the levels of circulating catechin compositions must be maintained above some minimum therapeutic dose to reduce the number of cancer cells and/or prevent cancer. In one embodiment, the reduction in the number of cancer cells is a result of cell death or apoptosis. In another embodiment, the reduction in the number of cancer cells is a result of inhibition of cell growth. In yet another embodiment, the reduction in the number of cancer cells is a result of cell growth arrest.

All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: (1) extended activity of the composition; (2) reduced dosage frequency; and (3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

Data showing the effectiveness of a sustained release formulation on the inhibition of NADH oxidase activity in cancer cells is presented in Section 9, infra.

5.5.2. Modes of Administration of Water-soluble Complexes

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

5.5.3. Oral Administration

For oral administration, the pharmaceutical preparation may be in liquid form, (e.g., solutions, syrups or suspensions), or may be presented as a drug product (e.g., capsule or powder) for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods wellknown in the art. In a preferred embodiment, the pharmaceutical composition may take the form of a capsule or powder to be dissolved in a liquid for oral consumption.

Preparations for oral administration may be suitably formulated to give controlled release of the active compound. In a preferred embodiment, the compounds of the present invention are formulated as controlled release powders of discrete micro-particles which can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33–45 of U.S. Pat. No. 5,354,556 which is incorporated by reference in its entirety. Particularly suitable polymers include those described, but not limited to, those described in column 3, line 46-column 4, line 8 of U.S. Pat. No. 5,354,556 which is incorporated by reference in its entirety.

5.5.4. Buccal Administration

For buccal administration, the compositions may take the form of tablets or lozenges formulated in conventional manner.

5.5.5. Parenteral Administration

The sustained release compounds of the invention may be formulated for parenteral administration, e.g., by intramuscular injections or implants for subcutaneous tissues and various body cavities and transdermal devices.

Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In a preferred embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil solutions and suspensions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachnis, maize, almond, cottonseed, and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

5.5.6. Rectal Administration

The compounds may also be formulated in rectal compositions such as suppositories or retention enemas, e.g., containing conventional suppository bases such as cocoa butter or other glycerides.

5.5.7. Packs and Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers having therapeutically or prophylactically effective amounts of the catechin complexes in pharmaceutically acceptable form. The catechin complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of catechin complexes by a clinician or by the patient.

5.6. Dosage

5.6.1. Catechins as a Dietary Supplement for Preventing Cancer

In one embodiment of this invention, a sustained release formulation comprising catechins may be used as a dietary or nutritional supplement for the prevention of cancer. In this embodiment, the total daily dose ranges of the active catechins for the conditions described herein are generally from about 10 mg to about 800 mg administered in divided doses administered parenterally or orally. A preferred total daily dose is from about 50 mg to about 400 mg of the active catechins.

In a another embodiment, a total daily dose of a sustained release formulation may be used as a dietary supplement is about 10 mg to about 800 mg of active catechins administered twice daily (e.g., in the morning and the evening) at a dose of about 5 mg to about 400 mg. The dosage forms and compositions may comprise any of the forms and compositions described supra. In a preferred embodiment, the sustained release formulation comprising catechins is a tablet, capsule, gel, or a liquid-soluble powder.

5.6.2. Catechins as a Therapeutic for Treating Cancer

In another embodiment of the invention, the magnitude of a therapeutic dose of catechins in the acute or chronic management of cancer will vary with the severity of the condition to be treated and the route of administration. The dose, and dose frequency, will also vary according to the age, body weight, condition and response of the individual patient, and the particular catechin combination used. All combinations described in the specification are encompassed as therapeutic, active catechin mixtures and it is understood that one of skill in the art would be able to determine a proper dosage of particular catechin mixtures using the parameters provided in the invention. In general, the total daily dose ranges of the active catechins for the conditions described herein are generally from about mg to about 1000 mg administered in divided doses administered parenterally or orally or topically. A preferred total daily dose is from about 200 mg to about 600 mg of the active catechins.

For example, in one embodiment, the daily dose ranges of EGCg and EC for the conditions described herein are generally from about 0.15 to about 15 mg per kg body weight of EGCg and 10 to about 100 mg per kg weight of body EC. Preferably the catechin formulation of the invention is given daily until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechins are not particularly toxic, the formulation may be administered for as long as necessary to achieve the desired therapeutic effect.

In the case where an intravenous injection or infusion composition is employed, a suitable dosage range for use is, e.g., from about 0.01 to about 1.5 mg per kg body weight of EGCg and about 1 to about 10 mg per kg body weight of EC total daily.

For treatment of solid tumors, a preferred dosing regimen involves intravenous infusion of about 0.01 to about 1.5 mg per kg body weight of EGCg and about 1 to about 10 mg per kg body weight of EC per day. This daily treatment protocol is repeated once per month until the tumor growth tumor is inhibited or when the tumor shows signs of regression.

As stated in Section 5.1, EGCg and EC are present in varying percentages in the formulation. Thus, the formulation will be adjusted to reflect the concentrations of EGCg and EC, i.e., in one preferred embodiment, EGCg is 40% and EC is 7% of the total catechins in the formulation. So, in one non-limiting example, 15 to 1500 mg of the total formulation will be required for a dose of 6 to 600 mg of EGCg and 1 to 105 mg of EC.

In another preferred embodiment, EGCg is 0.1% of the total catechins and EC is 100 fold greater than the EGCg content of the total catechins in the formulation. So, in this non-limiting example, 15 to 1500 mg of the total formulation will be required for a dose of 0.15 to 1.5 mg of EGCg and 1.5 to 150 mg of EC.

In an alternative embodiment of the invention, the effect of the therapy with EGCg and EC on cancer treatment can be monitored by any methods known in the art, including but not limited to monitoring circulating tNOX activity in patient sera, as well as more traditional approaches such as determining levels of tumor specific antigens and putative biomarkers, e.g., carcinoembryonic antigens (CEA), alpha-fetoprotein; and changes in morphology and/or size using computed tomographic scan and/or sonogram.

Desirable blood levels may be maintained by a continuous infusion of EGCg and EC as ascertained by plasma levels. It should be noted that the attending physician would also know how to and when to adjust treatment to higher levels if the clinical response is not adequate (precluding toxic side effects, if any).

Again, any suitable route of administration may be employed for providing the patient with an effective dosage of EGCg and EC or another catechin combination of this invention. Dosage forms include tablets, troches, cachet, dispersions, suspensions, solutions, capsules, gel caps, caplets, compressed tablets, sustained release devices, patches, and the like.

The pharmaceutical compositions of the present invention comprise catechins as the active ingredients, as well as pharmaceutically acceptable salts thereof, and may also contain a pharmaceutically acceptable carrier, and optionally, other therapeutic ingredients. The term "pharmaceutically acceptable salts" refers to salts prepared from pharmaceutically acceptable non-toxic acids and bases, including inorganic and organic acids and bases.

The pharmaceutical compositions include compositions suitable for oral and parenteral (including subcutaneous, intramuscular, intrathecal, intravenous, and other injectables) routes, although the most suitable route in any given case will depend on the nature and severity of the condition being treated.

In addition, the catechin carrier could be delivered via charged and uncharged matrices used as drug delivery devices such as cellulose acetate membranes, also through targeted delivery systems such as fusogenic liposomes attached to antibodies or specific antigens.

In practical use, catechins can be combined as the active ingredient(s) in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, micro-crystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% (w/v), normal saline or other solutions. The total dose of the catechins may be administered in a vial of intravenous fluid, e.g., ranging from about 0.01 to about 1000 mg per kg body weight of catechins. The volume of dilution fluid will vary according to the total dose administered and over the length of the period of time of administration.

An exemplary course of treatment of a patient with cancer or solid cancer can involve daily administration by intravenous infusion of catechins in an aqueous solution at a daily dose of about 0.01 to about 1.5 mg of the EGCg and about 1 to about 10 mg of the EC compositions per kg of body weight of the patient. The course of treatment may be repeated for up to ten times over approximately 10 months with a break of about three to six weeks in between courses. The post-remission course of treatment involves infusion of EGCg and EC at a daily dose of about 0.01 to about 1 mg per kg of body weight of the patient on a daily or weekdays-only basis for a cumulative total of 25 days.

In another embodiment, the invention encompasses the daily dose ranges of EGCg and ECG for the conditions described herein are generally from about 0.1 to about 15 mg per kg body weight administered in divided doses administered orally. Preferably the catechin formulation of the invention is given daily, or until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechins are not particularly toxic, the formulation may be administered for as long as necessary to achieve the desired therapeutic effect. In the case where an intravenous injection or infusion composition is employed, a suitable dosage range for use is, e.g., from about 0.01 to about 1.5 mg per kg body weight of EGCg and ECG total daily.

For treatment of solid tumors, a preferred dosing regimen involves intravenous infusion of the active catechins of the invention, as described above, in the amount of about 0.01 to about 10 mg per kg body weight per day. This daily treatment protocol is repeated once per month until the tumor growth tumor is inhibited or when the tumor shows signs of regression.

As stated in Section 5.1, EGCg and ECG are present in varying percentages in the formulation. Thus, the formulation will be adjusted to reflect the concentrations of EGCg and ECG, i.e., in a preferred embodiment, EGCg is 40% and ECG is 15% of the total catechins in the formulation. Thus, in one non-limiting example, 15 to 1500 mg of the total formulation will be required for a dose of 6 to 600 mg of EGCg and 2.25 to 225 mg of ECG.

The effect of the therapy with EGCg and ECG on cancer treatment can be monitored by methods stated supra in the example of EGCg and EC. Similarly, pharmaceutical compositions and routes of administration are similar as those described supra for EGCg and EC.

For the purposes described above, the invention also encompasses methods for monitoring patient response to tea catechins. By monitoring circulating tNOX activity in patient sera, it will be possible to determine therapeutic dosages and to monitor therapeutic benefit from tea catechins. The response of neoplastic cells to the subject compositions may be monitored by assaying the blood or urine of the patient for the NOX activity that is responsive to the catechin compositions, i.e., tNOX. Various assays may be used to monitor activity, such as a NOX assay for neoplasia determination see e.g., U.S. Pat. No. 5,605,810. By following the above monitoring procedures, an effective dosage of the subject compositions may be administered in accordance with the requirement of an individual patient.

6. EXAMPLE

Epigallocatechin Gallate Inhibits Preferentially the Nadh Oxidase and Growth of Transformed Cells in Culture

6.1. Materials and Methods 6.1.1. Growth of Cells

HeLa (ATCC CCL2) cells were grown in 175 $cm^2$ flasks in Minimal Essential Medium (Gibco), pH 7.4, at 37° C. with 10% bovine calf serum (heat-inactivated), plus 50 mg/l gentamycin sulfate (Sigma). Cells were harvested by scraping and taken up in 140 mM NaCl, 5 mM KCl, 0.7 mM $Na_2HPO_4$ and 25 mM Tris, pH 7.4 to a final cell concentration of 0.1 g wet weight (gww) per ml.

MCF-10A human mammary epithelial cells were cultured in a 1:1 mixture of Ham's F12 medium and Dulbecco's Modified Eagle's medium containing cholera enterotoxin (100 ng/ml), insulin (10 μg/ml), hydrocortisone (0.5 μg/ml), epidermal growth factor (EGF, 20 mg/ml), and 5% horse serum. Media were renewed every 2–3 days.

BT-20 human breast adenocarcinoma cells were cultured in Eagle's minimal essential medium nonessential amino acids and Eagle's balanced salts supplement with 10% fetal bovine serum. Media were renewed as for MCF-10A cells.

Cell lines were from the American Type Culture Collection (Rockville, Md.).

6.1.2. Purification of Plasma Membranes from Cultured Cells

Cultured cells were collected by centrifugation for 6–15 min at 175–1000×g. The cell pellets were resuspended in 0.2 mM EDTA in 1 mM NaHCO$_3$ in an approximate ratio of 1 ml per 10$^8$ cells and incubated on ice for 10–30 min to swell the cells. Homogenization was achieved in 7- to 8-ml aliquots with a Polytron homogenizer (Brinkmann) for 30–40 sec at 10,500 rpm, using a PT-PA 3012/23 or ST-10 probe. To estimate breakage, the cells were monitored by light microscopy before and after homogenization. At least 90% cell breakage without breakage of nuclei was achieved routinely.

The homogenates were centrifuged for 10 min at 175×g to remove unbroken cells and nuclei and the supernatant was centrifuged a second time at 1.4×10$^6$ g min (e.g., 1 h at 23,500×g) to prepare a plasma membrane-enriched microsome fraction. The supernatant was discarded and the pellets were resuspended in 0.2 M potassium phosphate buffer in a ratio of ~1 ml per pellet from 5×10$^8$ cells. The resuspended membranes were then loaded onto the two-phase system constituted on a weight basis consisting of 6.6% (w/w) Dextran T-500 (Pharmacia) and 6.6% (w/w) Polyethylene Glycol 3350 (Fisher) in a 5 mM potassium phosphate buffer (pH 7.2) for aqueous two-phase separation as described (Morré 1971, Methods Enzymol. 22:130–148, and Morré and Morré, 1989, BioTechniques 7:946–958). The upper phase, enriched in plasma membranes, was diluted 5-fold with 1 mM sodium bicarbonate and the membranes were collected by centrifugation. The purity of the plasma membrane was determined to be >90% by electron microscope morphometry. The yield was 20 mg plasma membrane protein from 10$^{10}$ cells.

6.1.3. Preparation of HeLa cells and cell-free extracts

HeLa S cells were collected by centrifugation and shipped frozen in 0.1 M sodium acetate, pH 5 in a ratio of 1 ml packed cell volume to 1 ml of acetate (Cellex Biosciences, Minneapolis, Minn.). The cells were thawed at room temperature, resuspended and incubated at 37° C. for 1 h to release the protein (del Castillo-Oliveras et al., 1998, Arch. Biochem. Biophys. 358:125–140). The cells were removed by centrifugation at 37,000 g for 60 min and the cell-free supernatants were refrozen and stored in 1 ml aliquots at −70° C.

For heat treatment, 1 ml aliquots of the above supernatant material were thawed at room temperature and heated to 50° C. for 10 min. The denatured proteins were removed by centrifugation (1,500 g, 5 min). Full activity was retained from this step (del Castillo-Oliveras et al., 1998, Arch. Biochem. Biophys. 358:125–140).

For protease treatment, the pH of the heat-stable supernatant was adjusted to 7.8 by addition of 0.1 M sodium hydroxide. *Tritirachium album* proteinase K (Calbiochem) was added (4 ng/ml) and incubated at 37° C. for 1 h with full retention of enzymatic activity and drug response (del Castillo-Oliveras et al., 1998, Arch. Biochem. Biophys. 358:125–140). The reaction was stopped either by freezing for determination of enzymatic activity or by addition of 0.1 M phenylmethylsulfonyl fluoride (PMSF) in ethanol to yield a final concentration of 10 mM PMSF.

6.1.4. Spectrophotometric Assay of NADH Oxidase

NADH oxidase activity was determined as the disappearance of NADH measured at 340 nm in a reaction mixture containing 25 mM Tris-Mes buffer (pH 7.2), 1 mM KCN to inhibit low levels of mitochondrial oxidase activity, and 150 mM NADH at 37° C. with stirring. Activity was measured using a Hitachi U3210 or SLM Aminco DW2000 spectrophotometer with continuous recording over two intervals of 5 min each. A millimolar extinction coefficient of 6.22 was used to determine specific activity. EGCg was added at the final concentrations indicated at the beginning of the assay and was present during the assay period.

Proteins were estimated by the bicinchonic acid method (Smith et al., 1985, Anal. Biochem. 150:76–85) with bovine serum albumin as standard.

6.1.5. Fluorescence Microscopy

Cells were grown for 72 h on glass coverslips placed in small culture dishes with media containing 100 μM EGCg in ethanol or an equivalent amount of ethanol alone. The coverslips were rinsed and the cells fixed in methanol followed by addition of fluorescent dye 4',6-diamidino-2-phenylindole (DAPI) as described (Wolvetang et al., 1994, FEBS Lett. 339:40–44). Cells were observed and photographed at a primary magnification of 400×.

6.1.6. Determination of EGCg

EGCg was determined with the hot water extracts using the standardized chromatographic procedure described by Katiyar et al. (Katiyar et al., 1992, Nutr. Can. 18:73–83). Authentic EGCg (Sigma) was used as the standard.

6.1.7. Chemicals

All chemicals were from Sigma (St. Louis, Mo.) unless otherwise specified. EGF was from mouse, culture grade, from Upstate Biotechnology Inc. (Lake Placid, N.Y.). Tea infusions were prepared by sequential steeping of ca. 2-g bags of tea (Lipton) in 10 ml of water for 10 min each. At the end of the infusion, bags were pressed to remove liquid.

6.2. Results 6.2.1. NADH Oxidase Activity in Plasma Membrane Vesicles

Epigallocatechin gallate (EGCg) was without effect on the NADH oxidase activity of plasma membrane vesicles (FIG. 2) or NADH oxidase solubilized and partially purified from the cell surface (FIG. 3) of human mammary epithelia (MCF-10A). However, with plasma membranes from human mammary adenocarcinoma (BT-20) or HeLa (human cervical carcinoma) cells, NADH oxidase activities were inhibited by 30 to 40% with an ED$_{50}$ of about 1 nM (FIG. 2). BT-20 and HeLa cells contain a drug-responsive component of NADH oxidase activity inhibited by capsaicin or the antitumor sulfonylurea as well as NADH oxidase activities resistant to inhibition. The responses to EGCg were comparable to those for capsaicin and the sulfonylurea.

With plasma membrane vesicles from the BT-20 mammary adenocarcinoma cell line, the NADH oxidase specific activity was approximately 1.5 that of the MCF-10A cell line (FIG. 2A). Upon addition of EGCg, the specific activity of the MCF-10A cells was unchanged, whereas, that of the BT-20 was reduced to approximately the same level as that of the MCF-10A cells (FIG. 2A). Also inhibited by EGCg in a similar fashion was the NADH oxidase activity from plasma membranes of HeLa cells (FIG. 2B). Thus, in the plasma membrane vesicles from the BT-20 and HeLa cells, there were both EGCg-resistant and EGCg-susceptible components whereas in the plasma membrane vesicles from the MCF 10A cells only an EGCg-resistant activity was observed (FIG. 2A).

6.2.2. NADH Oxidase Activity Released from Cultured Cells

Results similar to those observed with isolated plasma membrane vesicles were obtained as well with solubilized NADH oxidase preparations of NADH oxidase released from cultured cells by low pH treatment (FIG. 3). With BT-20 (FIG. 3A) and HeLa (FIG. 3B) preparations, activity was strongly inhibited by EGCg with an $EC_{50}$ of between 1 and 10 nM. The released and solubilized NADH oxidase for the MCF-10A cells was much less affected by the EGCg (FIG. 3A). As with isolated plasma membrane vesicles, the specific activity of the released NADH oxidase preparations from BT-20 cells was greater (approximately twice) than that of the released preparations from MCF-10A cells. Following treatment with EGCg, the specific activity of the preparations from BT-20 cells was reduced to a level comparable to the specific activity of the preparations from MCF-10A cells. Thus, the EGCg appears to inhibit specifically the drug-responsive NADH oxidase component of the tumorigenically transformed cell lines but not that of the constitutive NADH oxidase activity of the MCF-10A mammary epithelial line.

6.2.3. Effect of EGCg on Intact Cells in Culture

EGCg also inhibited the growth of the BT-20 mammary adenocarcinoma and HeLa cells in culture (FIGS. 2C, D). While not as striking as for the inhibition of NADH oxidase, EGCg did preferentially restrict the growth of the HeLa and BT-20 cells compared to MCF-10A (FIGS. 2C, D). Growth of the MCF-10A mammary epithelial cells was unaffected by EGCg except at very high doses of $10^{-4}$ M (FIG. 2C), whereas that of the tumorigenically transformed BT-20 and HeLa cells was 50% inhibited at about $5\times10^{-3}$ M (FIGS. 2C, D).

Despite early growth inhibition of MCF-10A cells by EGCg, the cells quickly recovered and eventually grew normally (FIG. 4). This is in contrast to HeLa and BT-20 cells where the cells did not recover and died (FIG. 4).

Measurements of the diameters of treated HeLa and BT-20 cells taken directly from printed micrographs revealed that, on average, the cells treated with $5\times10^{-6}$ to $5\times10^{-5}$ M EGCg exhibited volumes ~50% those of untreated cells. At $10^{-6}$ M EGCg, there was no response of any of the cell lines at 72 h despite the fact that this EGCg concentration inhibited the tNOX activity of isolated plasma membranes. The possibility was considered that the combination of a reversible inhibition and rapid metabolism of EGCg might result in an overall lack of growth inhibition at $10^{-6}$ M EGCg after 3 days. To test this possibility, cells were treated with $10^{-6}$ M EGCg twice daily for 96 h after which time the cells were photographed, measured and counted. Cell diameters were reduced on average by about 25% and cell volume by 50% by the twice daily $10^{-6}$ M EGCg dosage. Cell number also was reduced by about 25% with both HeLa and BT-20 cells by the $10^{-6}$ M EGCg provided twice daily whereas with the non-cancer MCF-10A cells, growth rate and cell diameters were unaffected or slightly increased. When the cells treated with $10^{-5}$ or $5\times10^{-5}$ EGCg were stained to reveal DAPI fluorescence, a very large percentage of the treated cells showed nuclear DNA with the condensed and fragmented appearance characteristic of a poptotic cells (FIG. 5).

10 6.2.4. Green Tea Inhibits NADH Oxidase

Since EGCg is considered as one of the major compounds contributing to the cancer preventative actions attributed to green tea, green tea infusions were examined as well for their ability to inhibit the NADH oxidase (Weisburger, 1997, Can. Lttr. 114:315–317; Chen et al., 1998, Can. Lttr. 129:173–179; Fujiki et al., 1998, Mutation Res. 402:307–310; Liao et al., 1995; Can. Lttr. 96:239–243; Stoner and Mukhtar, 1995, J. Cell. Biochem. 22:169–180; and Ahmad et al., 1997, J. Nat. Can. Inst. 89:1881–1886). Both the solubilized and partially purified NADH oxidase released from cells by low pH treatment (FIG. 6) and the NADH oxidase of sera pooled from cancer patients (Table 1) were inhibited by green tea infusions. Infusions of green tea (Lipton) were approximately ten times more effective than those of black tea (Lipton) and correlated approximately with the content of EGCg with an $EC_{50}$ of $2\times10^{-6}$ M EGCg equivalent to 1 µg/ml.

TABLE 1

Inhibition of tNOX activity by tea infusions and by epigallocatechin gallate (EGCg), the major tea polyphenol (catechin) of green tea, for sera pooled from patients with cancer. The EGCg content was determined as described (Katiyar et al., 1992, Nutr. Can. 18:73–83). Results were repeated 3 to 5 times with different sources and preparations of both black and green tea and with consistent findings.

| Source | $EC_{50}$ | EGCg (µg/ml) |
|---|---|---|
| Black tea (Lipton) | 1:10 to 1:100 | 1 |
| Green tea (Lipton) | 1:1000 | 1 |
| Epigallocatechin gallate (EGCg) | $2\times10^{-6}$ M | 1 |

6.2.5. EGCg Inhibits Cancer Cell Growth

Not only did EGCg inhibit the NADH oxidase of plasma membrane vesicles from cancer cells and not that of normal cells, the substance exerted a parallel response on growth. Growth of HeLa cells was almost completely inhibited by EGCg whereas growth of CHO cells and mammary epithelial cells was much less affected by EGCg. With treated HeLa cells, nuclei exhibited patterns of fluorescence characteristic of apoptosis (Smith et al., 1985, Anal. Biochem. 150:76–85). Thus, the cyanide-resistant NADH oxidase of the plasma membrane appears to represent an enzymatic activity whose inhibition by EGCg correlates with an inhibition of growth and subsequent apoptosis in susceptible cancer cell lines.

7. EXAMPLE

Synergistic Effects of (–)-Epigallocatechin Gallate With (–)-Epicatechin on Inhibition of Cell Surface Nadh Oxidase (NOX) Activity and Growth of 4T1 Mouse Mammary and Hela Cells in Culture

7.1. Materials and Methods

7.1.1. Chemicals

EGCg and EC were purchased from Sigma (St. Louis, Mo.) or purified from leaves of green tea and supplied by Pharmanex (Brisbane, Calif.). The stability and purity (>98%) of the EGCg and EC were confirmed by high performance liquid chromatographic analysis.

7.1.2. Growth of cells

HeLa (ATCC CCL2) cells were grown in 150 cm² flasks in Minimal Essential Medium (Gibco), pH 7.4, at 37° C. with 10% bovine calf serum (heat-inactivated), plus 50 mg/l gentamicin sulfate (Sigma). Cells were trypsinized with Sigma IX trypsin for 1 to 2 min and harvested by scraping and taken up in 140 mM NaCl, 5 mM KCl, 0.7 mM Na₂HPO₄ and 25 mM Tris, pH 7.4, to a final cell concentration of 0.1 g wet weight (gww) per ml.

A mouse mammary tumor subpopulation line 4T1 arising from a BALB/cf C3H mouse was grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 µg/ml) (Milleret al., 1987, Brit. J. Can. 56:561–569 and Miller et al., 1990, Invasion Metastasis 10:101–112).

7.1.3. Purification of plasma membranes from cultured cells

Cultured cells were collected by centrifugation for 6 to 15 min at 1,000 to 3,000 rpm. The cell pellets were resuspended in 0.2 mM EDTA in 1 mM $NaHCO_3$ in an approximate ratio of 1 ml per $10^8$ cells and incubated on ice for 10 to 30 min to swell the cells. Homogenization was with a Polytron Homogenizer for 30 to 40 sec at 10,500 rpm using a PT-PA 3012/23 or ST-probe in 7 to 8 ml aliquots. To estimate breakage, the cells were monitored by light microscopy before and after homogenization. At least 90% cell breakage without breakage of nuclei was achieved routinely.

The homogenates were centrifuged for 10 min at 175 g to remove unbroken cells and nuclei and the supernatant was centrifuged a second time at 1.4×10 g. min (e.g., 1 h at 23,500 g) to prepare a plasma membrane-enriched microsome fraction. The supernatant was discarded and the pellets were resuspended in 0.2 M potassium phosphate buffer in a ration of approximately 1 ml per pellet from $5\times10^8$ cells. The resuspended membranes were then loaded onto the two-phase system constituted on a weight basis. The two-phase system contained 6.4% (w/w) Dextran T-500 (Pharmacia), 6.4% (w/w) Polyethylene Glycol 3350 (Fisher), and 5 mM potassium phosphate, pH 7.2 (Morré and Morré, 1989, BioTechniques 7:946–958). The homogenate (1 g) was added to the two-phase system and the weight of the system was brought to 8 g with distilled water. The tubes were inverted vigorously for 40 times in the cold (4° C.). The phases were separated by centrifugation at 750 rpm (150×g) in a Sorvall HB 4 rotor for 5 min. The upper phases were withdrawn carefully with a Pasteur pipette, divided in half and transferred into 40 ml plastic centrifuge tubes. The tube contents were diluted with cold 1 mM $NaHCO_3$ and collected by centrifugation at 10,000×g in a HB rotor for 30 min. Plasma membrane pellets were resuspended in 50 mM Tris-Mes buffer (pH 7.2) and stored at −70° C. Proteins were determined using the bicinchoninic acid (BCA) assay (Smith et al., 1985, Anal. Biochem. 100:76–85) with bovine serum albumin as standard. The upper phase, enriched in plasma membranes, was diluted 5-fold with 1 mM sodium bicarbonate and the membranes are collected by centrifugation. The purity of the plasma membrane was determined to be >90% by electron microscope morphometry. The yield was 20 mg plasma membrane protein from $10^{10}$ cells.

7.1.4. Spectrophotometric assay of NADH oxidase

NADH oxidase activity was determined as the disappearance of NADH measured at 340 nm in a reaction mixture containing 25 mM Tris-Mes buffer (pH 7.2), 1 mM KCN, and 150 µM NADH at 37° C. Activity was measured using a Hitachi U3210 spectrophotometer with stirring and continuous recording over two intervals of 5 min each. A millimolar extinction coefficient of 6.22 was used to determine specific activity.

7.2. Results 7.2.1. Effect of EGCg and EC on solubilized NOX

Mixtures of EGCg with EC were tested first with a NOX preparation solubilized from HeLa cells (FIG. 7) and subsequently with cells. With the solubilized NOX protein, maximum inhibition was achieved by a mixture of $10^{-9}$ M EGCg plus $5\times10^{31\,6}$ M EC. Neither EC alone (up to and including $10^{-4}$ M) nor $10^{-9}$ M EGCg were effective in inhibiting the activity of the solubilized plasma membrane NADH oxidase protein.

Apoptosis was considerably enhanced by the combination of EGCg and EC (FIG. 8). In the absence of EC, 50% growth arrest by EGCg was observed at $10^{-5}$ M.

However, in the presence of $10^{-4}$ M EC, the concentration of EGCg for 50% growth arrest was lowered to $10^{-7}$ M and, in one experiment, the cells were totally killed by the combination of $10^{-7}$ M EGCg plus $10^{-4}$ M EC.

7.2.2. Effect of EGCg and EC on NOX in Intact Cells

A similar response was seen with the NADH oxidase activity of intact 4T1 cells (FIG. 9). With $10^{-4}$ M EC, $10^{-7}$ M EGCg, or no addition, the response was minimal. However, in the presence of $10^{-7}$ M EGCg, a substantial dose response to EC was observed.

Mouse 4T1 mammary carcinoma cells are particularly refractory to drug-induced growth inhibition and cell killing. However in the presence of the combination of $10^{-7}$ M EGCg and $10^{-4}$ M EC, the cells were killed (Table 2). This remarkable drug response was reflected in the inhibition of the oxidation of NADH by the intact 4T1 cells (Table 3, FIG. 9). The activity was completely inhibited back to basal levels by $10^{-7}$ M EGCg plus $10^{-4}$ M EC. The $EC_{50}$ for inhibition of the drug-responsive component of the plasma membrane NADH oxidase was $2\times10^{-9}$ M in the presence of $10^{-4}$ M EC alone, $10^{-7}$ M EGCg alone or $10^{-4}$ M EC+$10^{-7}$ M EGCg, the $EC_{50}$ for inhibition by EC was between $2\times10^{-9}$ M and $5\times10^{-8}$ M (Table 3).

TABLE 2

Killing of 4T1 metastatic mouse mammary cancer cells in culture.

| Addition | Increase in cell number $cm^{-2}$ over 72 h.$10^2$ |
|---|---|
| None | 550 |
| EGCg $10^{-7}$M | 520 |
| EC $10^{-4}$M | 560 |
| EGCg $10^{-7}$M + EC $10^{-4}$M | −40 * |

*100% Dead

TABLE 3

Preliminary Animal Study.
Balb/c mice, 4T1 mouse mammary cancer.
Treated for 5 days.

| Treatment | Amount/animal | Tumor wt (g) | Metastases to axillary nodes (Number of mice) | Lung Mets |
|---|---|---|---|---|
| Control (water only) | - - - | 2.3 ± 0.3 | +++ | + |
| Glaucarubolone (4 × $10^{-6}$M) | 1 mg | 1.5 ± 0.1 | +++ | + |
| EGCg $10^{-7}$M + EC $10^{-4}$M | 0.2 + 1.2 mg | 0.75 ± 0.35 | + | - - - |
| Glaucarubolone + EGCg + EC | 1 + 0.2 + 1.2 mg | 1.2 ± 0.4 | +++ | +* |

Each animal received 100 µl/day
*One animal with liver metastases

Epicatechin alone was largely without effect on the cell surface NADH oxidase of 4T-1 cells (FIG. 9, no addition) over the range $10^{-7}$ M to $10^{-4}$ M. However, in the presence of $10^{-7}$ M EGCg, the drug responsive component of the cell surface NADH oxidase was inhibited maximally at about $10^{-4}$ M with an $EC_{50}$ of about 2×10–7 M. The effect of EGCg was approximately the same as the concentration is increased up to $10^{-4}$ M (Table 4). The $EC_{50}$ was increased slightly at $10^{-5}$ and $10^{-4}$ M EGCg although the difference is not significant. The forms of the dose response curves including maximum inhibition were unchanged from that with $10^{-7}$ M EGCg and only a function of the concentration of EC (FIG. 10).

TABLE 4

$EC_{50}$ for (−)-epicatechin in the presence of varying concentrations of EGCg alone or supplied as Tegreen ™ on the inhibition of tNOX activity of intact 4T1 mouse mammary cells in culture.

| EGCg concentration, | $EC_{50}$ for tNOX inhibition by (−)-epicatechin, $10^{-6}$ M | |
|---|---|---|
| M | EGCg | Tegreen ™ |
| 0 | No effect | No effect |
| $10^{-8}$ | No effect | No effect |
| $10^{-7}$ | 0.2 ± 0.1 | No effect |
| $10^{-6}$ | 0.15 ± 0.05 | 0.5 ± 0.4 |
| $10^{-5}$ | 0.7 ± 0.3 | 0.4 ± 0.1 |
| $10^{-4}$ | 0.5 ± 0.4 | 0.3 ± 0.2 |

7.2.3. Effect of Tegreen™ on NOX in Intact Cells With a commercially supplied tea concentrate (Tegreen™, Pharmanex, Brisbane, Calif.), results were similar except that on an EGCg basis a higher concentration of Tegreen™ was required to achieve the same response (Table 4). With Tegreen™, an EGCg equivalent concentration of $10^{-6}$ M was required to elicit the response and $10^{-7}$ M was largely without effect or slightly stimulatory (FIG. 11, upper curve). Tegreen™ alone tended to stimulate the surface NADH oxidase activity of the intact 4T1 cells but the dose response with respect to EC was similar to that when EGCg in the absence of other tea constituents was added (FIG. 11, lower curve). The $EC_{50}$ for inhibition of activity by EC was $0.4 \pm 0.1 \times 10^{-7}$ M comparing $10^{-6}$, $10^{-5}$ and $10^{-4}$ M EGCg supplied as Tegreen™ (table 4).

With intact HeLa cells, the tNOX activity was maximally inhibited at $10^{-7}$ M to $10^{-6}$ M (FIG. 12). At $10^{-5}$ M EGCg or higher, NOX activity was stimulated. (−)-Epicatechin (EC) alone is without effect on NOX activity of HeLa cells (FIG. 13, upper curve). However, in the presence of $10^{-7}$ M EGCg, a further inhibitory response to EC was noted.

It should be noted that the formulation of Tegreen™ is an old formulation which is not encompassed within the scope of this invention. It should also be noted that the data suggested by the Tegreen™ experiments indicates that combinations of catechins are therapeutically more effective than EGCg alone on tNOX inhibition.

8. EXAMPLE

Synergistic Interaction of Different Tea Catechins with (−)-Epigallocatechin Gallate on Inhibition of Cell Surface Nadh Oxidase (NOX) Activity and Growth of 4T1 Mouse Mammary Cells in Culture

8.1. Materials and Methods 8.1.1. Chemicals

The (−)-epigallocatechin gallate (EGCg), (−)-epicatechin (EC), gallocatechin gallate (GCG) and ± catechin were purchased from Sigma (St. Louis, Mo.) or purified from leaves of green tea and supplied by Pharmanex (Brisbane, Calif.). The (−)-epigallocatechin (EGC) and (−)-epicatechin gallate (ECG) were purified from leaves of green tea and supplied by Pharmanex (Brisbane, Calif.). The stability and purity (>90%) of the catechins were confirmed by high performance liquid chromatographic analysis.

8.1.2. Growth of cells

A mouse mammary tumor subpopulation line 4T1 arising from a BALB/cf C3H mouse was grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 μg/ml) (Miller et al., 1987, Brit. J. Can. 56:561–569 and Miller et al., 1990, Invasion Metastasis 10:101–112).

8.1.2. Spectrophotometric assay of NADH oxidase

NADH oxidase activity was determined as the disappearance of NADH measured at 340 nm in a reaction mixture containing 25 mM Tris-Mes buffer (pH 7.2), 1 mM KCN, and 150 μM NADH at 37° C. Activity was measured at 340 nm with reference at 430 nm using an SLM Aminco DW-2000 spectrophotometer (Milton Roy, Rochester, N.Y.) in the dual beam mode of operation with stirring and continuous recording over two intervals of 5 min each. A millimolar extinction coefficient of 6.22 was used to determine specific activity.

8.2. Results 8.2.1. Effect of Catechin Combinations on NOX in Intact Cells Mixtures of EGCg with other catechins and mixtures of other catechins were tested for inhibition of tNOX activity intact with 4T1 mouse mammary carcinoma cells. Previously, maximum inhibition of the tNOX activity component was achieved by a mixture of $10^{-7}$ M EGCg plus $10^{-5}$ to $10^{-4}$ M EC. Neither EC alone (up to and including $10^{-4}$ M) nor EGCg (up to and including $10^{31\ 6}$ M) were effective in inhibiting the residual CNOX activity of the cells.

8.2.2. Effect of EGCg and EC on NOX in Intact Cells

These findings were extended to a more detailed comparison of different concentrations of EGCg in the presence of 0, $10^{-8}$, $10^{-6}$ and $10^{-4}$ M EC on the NOX activity of the 4T1 cells (Table 5). In the absence of EC, the $EC_{50}$ for tNOX inhibition by EGCg was about $10^{-8}$ M with >90% inhibition at $10^{-7}$ M. In the presence of $10^{-8}$ EC EGCg inhibition was little enhanced. However with both $10^{-6}$ and $10^{-4}$ M EC, the efficacy of EGCg inhibition was enhanced 10-fold or greater (Table 5). EC alone was largely without effect on tNOX activity of the 4T1 cells.

TABLE 5

$EC_{50}$ and $EC_{>90}$ for (−)-epigallocatechin gallate (EGCg) in the presence of varying concentrations of (−)-epicatechin (EC) on the inhibition of tNOX activity of intact cultured 4T1 mouse mammary carcinoma cells.

| EC concentration, | tNOX inhibition by (−)-epigallocatechin gallate (EGCg), M | |
|---|---|---|
| M | $EC_{50}$ | $EC_{>90}$ |
| 0 | $10^{-8}$ | $10^{-7}$ |
| $10^{-8}$ | $10^{-8}$ | $10^{-7}$ |
| $10^{-6}$ | $10^{-9}$ | $10^{-8}$ |
| $10^{-4}$ | $5 \times 10^{-10}$ | $10^{-8}$ |

8.2.3. Effect of Other Catechins and EGCg on NOX in Intact Cells

Several catechins and catechin mixtures were tested for their ability to replace the EC in the combination with 10–7 M EGCg. ECG (FIG. 14) and EGC (FIG. 15) both were effective in enhancing the inhibition by EGCg of tNOX activity of cultured 4T1 cells. The residual tNOX activity remaining after $10^{-7}$ M EGCg was inhibited 50% by $5 \times 10^{-7}$ and $10^{-6}$ M of ECG and EGC respectively (Table 6).

Gallocatechin gallate (GCG) (FIG. 16) was less effective due to a propensity of the GCG to stimulate activity as the concentrations of GCG exceeded $10^{-7}$ M in the mixture.

Catechin was largely without effect on the cell surface NADH oxidase of 4T1 cells over the range $10^{-7}$ M to $10^{-4}$ M both in the presence (FIG. 17) or absence (not shown) of $10^{-7}$ M EGCg. Unlike GCG, catechin did not stimulate NOX activity and therefore, may represent an activity-neutral catechin component. A mixture of equal parts of ECG, EGC, EC and catechin (FIG. 18) was approximately equivalent in effectiveness to EC, ECG or EGC alone. There appeared to be no marked enhancement of inhibition by the mixture compared to the individual components tested singly (Table 6).

TABLE 6

Estimated $EC_{50}$ and $EC_{>90}$ for different catechins and catechin mixtures in the presence of (−)-epigallocatechin gallate (EGCg) on the inhibition of the residual tNOX activity of intact cultured 4T1 mouse mammary carcinoma cells remaining after addition of 0.1 mM EGCg.

| Catechin | Inhibition of residual tNOX remaining in the presence of $10^{-6}$M EGCg | |
|---|---|---|
| | $EC_{50}$ | $EC_{>90}$ |
| Epicatechin gallate (ECG) | $5 \times 10^{-7}$ M | $10^{-6}$M |
| Epigallocatechin (EGC) | $10^{-7}$ M | $10^{-5}$M |
| Gallocatechin gallate (GCG) | Not reached due to stimulation | |
| Catechin (C) | Not reached due to lack of inhibition | |
| ECG + EGC + EC + C | $5 \times 10^{-7}$ M | $10^{-5}$M |
| Base-cleaved Tegreen ™ | $<10^{-7}$ M | $10^{-7}$M |

8.2.4. Effect of Tegreen™ on NOX in Intact Cells

When a commercially supplied tea concentrate (Tegreen™, Pharmanex, Brisbane, Calif.), was treated with NADH to cleave the gallate esters, results were similar (FIG. 19) except that on an EGCg basis less catechin was required to achieve the same response as compared to individual catechins (Table 6). With the hydrolyzed Tegreen M, >90% inhibition was achieved at an EGCg equivalent concentration of $10^{-7}$ M and with an $EC_{50}$ of less than $10^{-7}$ M. The hydrolyzate was largely without effect on CNOX. A control preparation containing an amount of NaCl equivalent to the salt concentration of the tNOX hydrolyzate was without effect on activity (not shown).

In this Example, the synergy in inhibition of tNOX activity of cultured 4T1 mouse mammary carcinoma cells between the most potent tea catechin EGCg and less potent tea catechins such as EC was confirmed. Additionally, an equivalency among the catechins (EC, EGC, ECG) in eliciting the synergistic response has been shown, which is of considerable importance in efforts to optimize tea catechin mixtures for use in cancer therapy.

9. EXAMPLE

Effect of a Sustained Release Formulation of Tegreen on Inhibition of Cell Surface NADH Oxidase (NOX) Activity, Growth of 4T1 Mouse Mammary and Hela Cells in Culture, and Transplanted Adenocarcinoma Tumors

9.1. Materials and Methods 9.1.1. Chemicals

A commercially supplied tea concentrate, Tegreen™, was supplied by Pharmanex (Brisbane, Calif.). Microencapsulated formulations of Tegreen™ were synthesized by Biodar (Yavne, Israel), and designated as P-3039, P-3041, and a sustained release formulation, known as P-3069.

The sustained release formulation (P-3069), was synthesized with a CapsuDar® SR microencapsulation to achieve a slow, or sustained release effect. In addition to the green tea extract, the sustained release formulation also contains the active ingredients microcrystalline cellulose, maltodextrine, ethylcellulose, and magnesium stearate. The EGCg content of this sustained release formulation is 28.5%.

9.1.2. Growth of Cells

HeLa (ATCC CCL2) cells were grown in 175 cm² flasks in Minimal Essential Medium (Gibco), pH 7.4, at 37° C. with 10% bovine calf serum (heat-inactivated), plus 50 mg/l gentamycin sulfate (Sigma). Cells were harvested by scraping and taken up in 140 mM NaCl, 5 mM KCl, 0.7 mM $Na_2HPO_4$ and 25 mM Tris, pH 7.4 to a final cell concentration of 0.1 g wet weight (gww) per ml.

A mouse mammary tumor subpopulation line 4T1 arising from a BALB/cf C3H mouse was grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 µg/ml) (Miller et al., 1987, Brit. J. Can. 56:561–569 and Miller et al., 1990, Invasion Metastasis 10:101–112).

9.1.3. Spectrophotometric Assay of NADH Oxidase

NADH oxidase activity was determined as the disappearance of NADH measured at 340 nm in a reaction mixture containing 25 mM Tris-Mes buffer (pH 7.2), 1 mM KCN, and 150 HM NADH at 37° C. Activity was measured using a Hitachi U3210 spectrophotometer with stirring and continuous recording over two intervals of 5 min each. A millimolar extinction coefficient of 6.22 was used to determine specific activity.

9.1.4. Experimental Metastasis in Mice

Female BALB/c mice (8 to 12 weeks old) were injected with cells from the tumor subpopulation line 4TO7 arising from a BALB/c C3H mouse (Miller et al., 1987, Brit. J. Can. 56:561–569). Cells from a monolayer culture were suspended in Hank's buffered salt solution and $1 \times 10^5$ cells were injected subcutaneously into the mice in a volume of 0.1 ml. Primary tumors were measured twice a week in two perpendicular dimensions using a vernier caliper. Catechin mixtures were administered intratumoral on alternate days beginning after palpable tumor masses are discernible. A5 15 days post tumor implantation, the mice were sacrificed and major organs (e.g., lung, liver, and lymph nodes) were examined for evidence of metastases.

9.2. Results 9.2.1. Need for a Sustained Release Formulation

As described supra, the effect of the catechins on the inhibition of cell growth and tNOX inhibition is reversible, i.e., if EGCg is removed, cancer cells resume normal rates of growth. As shown in FIG. 20, with repeat additions of 100 nM EGCg four times a day, growth was inhibited during the day but recovered during the night (16 hours). As a result, there was no apoptosis. However, when the dose of EGCg was increased to 1 µM provided twice daily to cells in culture, growth was inhibited and the resultant cells were smaller (data not shown).

Indications are that NOX activity and cell growth must be inhibited for approximately 72 hours or more to induce apoptosis. Even a modest 30% decrease in cell diameter might exert little or no effect in slowing of cell multiplication. It would appear that a nearly complete inhibition of the cell volume increase following division would be required to block cell proliferation. Thus, there exists a need for a sustained release formulation of catechins in order for apoptosis to occur.

9.2.2. Effect of Sustained Release Formulation on Cell Growth

The effect of the microencapsulated formulations of Tegreen™ on the growth of cancer cells is presented in Table 7. Dosages were administered every two hours four times a day over eight hours. The sustained release formulation inhibited the growth of both HeLa cells and 4T-1 mouse mammary tumor cells. The inhibition of HeLa cell growth by the sustained release formulation was similar to Tegreen™ and the other microencapsulated formulations tested. In contrast, two of the microencapsulated formulations of Tegreen™ were less effective at inhibiting 4T-1 cell growth than the Tegreen™ starting material. However, the sustained release formulation inhibited 4T-1 cell growth at a concentration similar to that of the Tegreen™ starting material.

TABLE 7

Effect of Tegreen ™ and microencapsulated Tegreen ™ formulations on HeLa cell and 4T-1 mouse mammary tumor cell growth.

| | Cells/cm$^2$ × 10$^2$ after 72 h | |
|---|---|---|
| Addition | HeLa cells ($10^{-5}$M of Tegreen ™ formulation added) | 4T-1 cells ($5 \times 10^{-5}$M of Tegreen ™ formulation added) |
| None | 260 | 892 |
| Tegreen ™ starting material | 132 | 16 |
| P-3039 | 135 | 492 |
| P-3041 | 191 | 720 |
| Sustained release | 164 | 15 ($10^{-4}$M of Tegreen ™ formulation added) |

9.2.3. Effect of Sustained Release Formulation on NOX

The effect of the Tegreen™ starting material and the microencapsulated Tegreen™ formulations on cell surface NOX in HeLa and 4T-1 cells is presented in Table 8. All of the microencapsulated formulations of Tegreen™, including the sustained release formulation, inhibited NOX activity in both HeLa and 4T-1 cells. All of the microencapsulated formulations were effective at concentrations less than or equal to the Tegreen™ starting material. Significantly, the sustained release formulation inhibited NOX activity in both HeLa and 4T1 cells and was effective at a concentration less than Tegreen™. Furthermore, the overall concentrations of active catechins in the microencapsulated formulations are less than the concentrations of active catechins, e.g., EGCg, in the data presented supra in Examples 6 to 8. In other words, the microencapsulated formulations contain approximately 70% active catechins, thus the actual concentration of active catechins will be less than the concentration of the microencapsulated formulation that is administered.

TABLE 8

Effect of microencapsulated Tegreens on NOX activity 24 hours post addition. The number of experiments (n) is indicated. The range of EC$_{50}$ values (if n > 1) is noted below.

| | EC$_{50}$ | |
|---|---|---|
| | HeLa cells | 4T-1 mouse mammary tumor cells |
| Tegreen ™ starting material | $10^{-7}$M$^{(a)}$ (n = 7) | $10^{-7(b)}$M (n = 5) |
| P-3039 | $10^{-7(c)}$M (n = 2) | $10^{-8}$M (n = 1) |
| P-3041 | $10^{-7}$M (n = 1) | $5 \times 10^{-8}$M (n = 1) |
| Sustained release | $10^{-8}$M (n = 1) | $10^{-8}$M$^{(d)}$ (n = 4) |

$^a$$10^{-8}$ to $5 \times 10^{-6}$M
$^b$$5 \times 10^{-8}$ to $5 \times 10^{-7}$M
$^c$$10^{-7}$ to $5 \times 10^{-7}$M
$^d$$10^{-8}$ to $2 \times 10^{-8}$M

9.2.4. Effect of Sustained Release Formulation on a Tumor

The effect of the microencapsulated sustained release Tegreen™ formulation on a transplantable 4T-1 mammary adenocarcinoma in a BALB/c mouse is shown in FIG. 21. The tumor resulted from a subcutaneous injection of a tumor subpopulation line. The tumor was treated with 100 µl of a 2.3 mg/ml suspension of the sustained release formulation. Whenever a small granule of the sustained release formulation was located within the tumor mass, cells that were several mm around the particle were killed. In between the particles, the tumor continued to grow. As shown in FIG. 21, this gave rise to the distinctive "lumpy" appearance of the tumor mass with growing areas not receiving Tegreen™ surrounded by areas receiving Tegreen™ that were killed. Thus, the sustained release formulation of Tegreen™ is effective for eradicating tumor cell growth.

In this example, a microencapsulated sustained release formulation of Tegreen™ has been shown to be effective over time (>72h) for the inhibition of both in vitro and in vivo cancer cell growth. Furthermore, this sustained release formulation is effective at a concentration less than an equivalent amount of Tegreen™ at inhibiting NOX in the cancer cells tested.

10. EXAMPLE

Method for the Encapsulation of Epigallocatechin Gallate

As described in Section 5.1.2, all known methods for encapsulation which are compatible with the properties of tea catechins are encompassed by this invention.

For example, a sustained release formulation is described in U.S. Pat. No. 4,710,384, which is incorporated herein by reference in its entirety. Using U.S. Pat. No. 4,710,384 as an example, a sustained release formulation of EGCg can be prepared in the following manner:

One kg of EGCg is coated in a modified Uni-Glatt powder coater with ethyl cellulose. The ethyl cellulose is type 10 ethyl cellulose obtained from Dow Chemical Company. The spraying solution comprises an 8 percent solution of the ethyl cellulose in 90 percent acetone to 10 percent ethanol. Castor oil is added as plasticizer in an amount equal to 20 percent of the ethyl cellulose present.

The spraying conditions are as follows:

| | | |
|---|---|---|
| (i) | Speed | 1 liter/hour |
| (ii) | Flap | 10–15 percent |
| (iii) | Inlet Temperature | 50° C. |
| (iv) | Outlet temp. | 30° C. |
| (v) | Percent of Coating | 17 percent |

The coated EGCg is sieved to particle sizes between 74–210 microns. Attention is paid to ensure a good mix of particles of different sizes within that range. 400 mg of the coated particles are mixed with 100 mg of starch and the mixture is compressed in a hand press to 1.5 tons to produce 500 mg tablets.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A composition of a sustained release formulation of tea catechins comprising tea catechins and at least one component which controls the release of said catechins, comprising EGCg and EC catechins wherein, EGCg comprises at least 0.01% of said catechins, and the EC content is at least 10 fold greater than the EGCg content.

2. A composition of a sustained release formulation of tea catechins comprising tea catechins and at least one component which controls the release of said catechins, comprising EC and EGCg wherein the EC content is at least 100 fold greater than the EGCg content.

3. A composition of a sustained release formulation of tea catechins comprising tea catechins and at least one component which controls the release of said catechins, comprising EC and EGCg wherein the EC content is at least 1000 fold greater than the EGCg content.

4. The composition of any one of claims 1, 2 or 3, wherein the composition is microencapsulated.

5. The composition of claim 4 wherein the composition is microencapsulated with microcrystalline cellulose, maltodextrine, ethylcellulose, and magnesium stearate.

6. The composition of any one of claims 1, 2 or 3 wherein the composition is formulated as an oral preparation.

7. The composition of claim 6 wherein the oral preparation comprises tablets, capsules, gelcaps, or powders.

8. The composition of any one of claims 1, 2 or 3 wherein the composition is formulated as a sterile preparation.

9. The composition of any one of claims 1, 2 or 3 wherein the composition is formulated as a parenteral solution.

10. The composition of any one of claims 1, 2 or 3 wherein the component is a polymer matrix, gel, permeable membrane, osmotic system, multilayer coating, microparticle, liposome, or microsphere.

11. The composition of claim 10 wherein the polymer matrix is cellulose.

12. The composition of claim 11 wherein the cellulose is hydropropylmethyl cellulose.

13. The composition of any one of claims 1, 2 or 3 wherein the component is a coating containing a plasticizer.

14. The composition of claim 13 wherein the plasticizer is about to percent of the coating.

15. The composition of claim 13 wherein the plasticizer is about 20 to 25 percent of the coating.

16. The composition of any one of claims 1, 2 or 3 wherein the composition further comprises an anti-cancer drug.

17. The composition of claim 16 wherein the anti-cancer drug is adriamycin, bullatacin, simalikalactone D, or glaucarubolone.

18. The composition of any one of claims 1, 2 or 3 wherein the composition is formulated as a pharmaceutical preparation.

19. The composition of claim 18 wherein the composition is a liquid.

20. The composition of claim 19 wherein the liquid is a solution, syrup, or suspension.

21. The composition of any one of claims 1, 2 or 3 wherein the composition further comprises a phaimaceutically acceptable carrier.

22. The composition of claim 21 wherein the composition is a liquid and the pharmaceutically acceptable carrier is a suspending agent, emulsifying agent, non-aqueous vehicle, or a preservative.

23. The composition of claim 21 wherein the composition is a tablet or a capsule and the pharmaceutically acceptable carrier is a binding agent, filler, lubricant, disintegrant, or a wetting agent.

24. The composition of any one of claims 1, 2 or 3 wherein the composition is formulated as a buccal solution.

25. The composition of any one of claims 1, 2 or 3 wherein the composition is formulated for rectal administration.

26. The composition of any one of claims 1, 2 or 3 wherein the composition is in a pack or a kit.

27. The composition of any one of claims 1, 2 or 3 wherein the composition is a dietary or nutritional supplement for preventing cancer.

28. The composition of claim 27 wherein the supplement is about 10 mg to 800 mg of said catechins administered twice daily.

29. The composition of any one of claims 1, 2 or 3 wherein the composition is a therapeutic for treating cancer.

30. The composition of claim 29 wherein the therapeutic is about 10 mg to about 100,000 mg of said catechins administered twice daily.

* * * * *